(12) United States Patent
Burbidge et al.

(10) Patent No.: US 8,858,943 B2
(45) Date of Patent: Oct. 14, 2014

(54) ANTIGEN BINDING PROTEINS

(75) Inventors: Stephen Anthony Burbidge, Harlow (GB); Ian Richard Catchpole, Stevenage (GB); Jonathan Henry Ellis, Stevenage (GB); Susannah Karen Ford, Stevenage (GB); Volker Germaschewski, Stevenage (GB); Umesh Kumar, Stevenage (GB); Karen Louise Philpott, Harlow (GB); Peter Ernest Soden, Stevenage (GB)

(73) Assignee: Glaxo Group Limited (GB)

( * ) Notice: Subject to any disclaimer, the term of this patent is extended or adjusted under 35 U.S.C. 154(b) by 842 days.

(21) Appl. No.: 12/679,917

(22) PCT Filed: Sep. 23, 2008

(86) PCT No.: PCT/EP2008/062652
§ 371 (c)(1),
(2), (4) Date: Oct. 11, 2010

(87) PCT Pub. No.: WO2009/040336
PCT Pub. Date: Apr. 2, 2009

(65) Prior Publication Data
US 2011/0064740 A1    Mar. 17, 2011

(30) Foreign Application Priority Data

Sep. 25, 2007 (GB) .................................. 0718737.0

(51) Int. Cl.
| | | |
|---|---|---|
| *A61K 39/395* | (2006.01) | |
| *A61K 35/30* | (2006.01) | |
| *A61K 35/44* | (2006.01) | |
| *C07K 16/18* | (2006.01) | |
| *A61K 39/00* | (2006.01) | |

(52) U.S. Cl.
CPC ............. *C07K 16/18* (2013.01); *C07K 2317/24* (2013.01); *C07K 2317/55* (2013.01); *C07K 2317/567* (2013.01); *A61K 2039/505* (2013.01)
USPC ................ 424/139.1; 424/141.1; 424/142.1; 424/145.1; 424/156.1; 514/8.3; 514/20.8

(58) Field of Classification Search
None
See application file for complete search history.

(56) References Cited

U.S. PATENT DOCUMENTS 7,892,544 B2 *  2/2011  Pfeifer et al. .............. 424/133.1
2006/0121039 A1    6/2006  Sharif

FOREIGN PATENT DOCUMENTS

| WO | WO 2006/039327 A  | 4/2006 |
| WO | WO 2006/039327 A2 * | 4/2006 |
| WO | WO 2006/083533 A  | 8/2006 |
| WO | WO 2007/113172    | * 10/2007 |
| WO | WO 2007/113172 A  | 10/2007 |

OTHER PUBLICATIONS

Wassaf et al., Analytical Biochem., 351: 241-253, Feb. 10, 2006.*
Petrukhin K., Expert Opinion on Therapeutic Targets, 11(5):625-639, published May 2007.*
Guo et al., PNAS, 104(33):13444-13449, Aug. 14, 2007.*
Frenkel et al., J Neuroimmunology, 88: 85-90, 1998.*
Takeshi Yoshida, et al., J. Clinical Investigation, pp. 2793-2800, Oct. 1, 2005.
Ding, et al., Vision Research, Pergamon Press, Oxford, GB, vol. 48, No. 3, pp. 339-345, Feb. 1, 2008.
Evan P Booy, et al., Archivum Immunologiae et Therapiae Experimentalis, Birkhaeuser-Verlag, Basel, Ch, vol. 54, No. 2, Apr. 1, 2006.

* cited by examiner

*Primary Examiner* — Daniel E Kolker
*Assistant Examiner* — Stacey N MacFarlane
(74) *Attorney, Agent, or Firm* — Jason C. Fedon; William T. Han

(57) ABSTRACT

The present invention relates to methods of treating diseases or disorders affecting the eye or optic nerve characterized by elevated β-amyloid levels or β-amyloid deposits, particularly age related macular degeneration and glaucoma type diseases and β-amyloid dependent cataract formation, with antigen binding proteins that bind β-amyloid peptide and in particular human β-amyloid peptide.

10 Claims, No Drawings

SEQUENCE LISTING

```
<160> NUMBER OF SEQ ID NOS: 44

<210> SEQ ID NO 1
<211> LENGTH: 5
<212> TYPE: PRT
<213> ORGANISM: Mouse

<400> SEQUENCE: 1

Asp Asn Gly Met Ala
 1               5

<210> SEQ ID NO 2
<211> LENGTH: 17
<212> TYPE: PRT
<213> ORGANISM: Mouse

<400> SEQUENCE: 2

Phe Ile Ser Asn Leu Ala Tyr Ser Ile Asp Tyr Ala Asp Thr Val Thr
 1               5                  10                  15

Gly

<210> SEQ ID NO 3
<211> LENGTH: 6
<212> TYPE: PRT
<213> ORGANISM: Mouse

<400> SEQUENCE: 3

Gly Thr Trp Phe Ala Tyr
 1               5

<210> SEQ ID NO 4
<211> LENGTH: 16
<212> TYPE: PRT
<213> ORGANISM: Mouse

<400> SEQUENCE: 4

Arg Val Ser Gln Ser Leu Leu His Ser Asn Gly Tyr Thr Tyr Leu His
 1               5                  10                  15

<210> SEQ ID NO 5
<211> LENGTH: 7
<212> TYPE: PRT
<213> ORGANISM: Mouse

<400> SEQUENCE: 5

Lys Val Ser Asn Arg Phe Ser
 1               5

<210> SEQ ID NO 6
<211> LENGTH: 9
<212> TYPE: PRT
<213> ORGANISM: Mouse

<400> SEQUENCE: 6

Ser Gln Thr Arg His Val Pro Tyr Thr
 1               5

<210> SEQ ID NO 7
<211> LENGTH: 16
<212> TYPE: PRT
<213> ORGANISM: Artificial Sequence
<220> FEATURE:
<223> OTHER INFORMATION: 16mer peptide containing residues 1-10 of beta
      amyloid peptide
<220> FEATURE:
```

```
<221> NAME/KEY: MOD_RES
<222> LOCATION: (16)...(0)
<223> OTHER INFORMATION: Biotinylated

<400> SEQUENCE: 7

Asp Ala Glu Phe Arg His Asp Ser Gly Tyr Gly Ser Gly Gly Ser Lys
 1               5                  10                  15

<210> SEQ ID NO 8
<211> LENGTH: 16
<212> TYPE: PRT
<213> ORGANISM: Artificial Sequence
<220> FEATURE:
<223> OTHER INFORMATION: 16mer peptide containing residues 1-9 of beta
      amyloid peptide
<220> FEATURE:
<221> NAME/KEY: MOD_RES
<222> LOCATION: (16)...(0)
<223> OTHER INFORMATION: Biotinylated

<400> SEQUENCE: 8

Asp Ala Glu Phe Arg His Asp Ser Gly Gly Ser Gly Ser Gly Ser Lys
 1               5                  10                  15

<210> SEQ ID NO 9
<211> LENGTH: 16
<212> TYPE: PRT
<213> ORGANISM: Artificial Sequence
<220> FEATURE:
<223> OTHER INFORMATION: 16mer peptide containing residues 1-8 of beta
      amyloid peptide
<220> FEATURE:
<221> NAME/KEY: MOD_RES
<222> LOCATION: (16)...(0)
<223> OTHER INFORMATION: Biotinylated

<400> SEQUENCE: 9

Asp Ala Glu Phe Arg His Asp Ser Gly Ser Gly Gly Ser Gly Gly Lys
 1               5                  10                  15

<210> SEQ ID NO 10
<211> LENGTH: 16
<212> TYPE: PRT
<213> ORGANISM: Artificial Sequence
<220> FEATURE:
<223> OTHER INFORMATION: 16mer peptide containing residues 1-7 of beta
      amyloid peptide
<220> FEATURE:
<221> NAME/KEY: MOD_RES
<222> LOCATION: (16)...(0)
<223> OTHER INFORMATION: Biotinylated

<400> SEQUENCE: 10

Asp Ala Glu Phe Arg His Asp Gly Ser Gly Gly Ser Gly Gly Ser Lys
 1               5                  10                  15

<210> SEQ ID NO 11
<211> LENGTH: 16
<212> TYPE: PRT
<213> ORGANISM: Artificial Sequence
<220> FEATURE:
<223> OTHER INFORMATION: 16mer peptide containing residues 1-6 of beta
      amyloid peptide
<220> FEATURE:
<221> NAME/KEY: MOD_RES
<222> LOCATION: (16)...(0)
<223> OTHER INFORMATION: Biotinylated

<400> SEQUENCE: 11

Asp Ala Glu Phe Arg His Gly Ser Gly Gly Ser Gly Gly Ser Gly Lys
```

```
                1               5                  10                  15
```

<210> SEQ ID NO 12
<211> LENGTH: 16
<212> TYPE: PRT
<213> ORGANISM: Artificial Sequence
<220> FEATURE:
<223> OTHER INFORMATION: 16mer peptide containing residues 1-5 of beta
      amyloid peptide
<220> FEATURE:
<221> NAME/KEY: MOD_RES
<222> LOCATION: (16)...(0)
<223> OTHER INFORMATION: Biotinylated

<400> SEQUENCE: 12

```
Asp Ala Glu Phe Arg Gly Ser Gly Gly Ser Gly Gly Ser Gly Ser Lys
 1               5                  10                  15
```

<210> SEQ ID NO 13
<211> LENGTH: 16
<212> TYPE: PRT
<213> ORGANISM: Artificial Sequence
<220> FEATURE:
<223> OTHER INFORMATION: 16mer peptide containing residues 1-4 of beta
      amyloid peptide
<220> FEATURE:
<221> NAME/KEY: MOD_RES
<222> LOCATION: (16)...(0)
<223> OTHER INFORMATION: Biotinylated

<400> SEQUENCE: 13

```
Asp Ala Glu Phe Gly Ser Gly Gly Ser Gly Gly Ser Gly Gly Ser Lys
 1               5                  10                  15
```

<210> SEQ ID NO 14
<211> LENGTH: 16
<212> TYPE: PRT
<213> ORGANISM: Artificial Sequence
<220> FEATURE:
<223> OTHER INFORMATION: 16mer peptide containing residues 1-3 of beta
      amyloid peptide
<220> FEATURE:
<221> NAME/KEY: MOD_RES
<222> LOCATION: (16)...(0)
<223> OTHER INFORMATION: Biotinylated

<400> SEQUENCE: 14

```
Asp Ala Glu Gly Ser Gly Gly Ser Gly Gly Ser Gly Gly Ser Gly Lys
 1               5                  10                  15
```

<210> SEQ ID NO 15
<211> LENGTH: 16
<212> TYPE: PRT
<213> ORGANISM: Artificial Sequence
<220> FEATURE:
<223> OTHER INFORMATION: 16mer peptide containing residues 1-12 of beta
      amyloid peptide
<220> FEATURE:
<221> NAME/KEY: MOD_RES
<222> LOCATION: (16)...(0)
<223> OTHER INFORMATION: Biotinylated

<400> SEQUENCE: 15

```
Asp Ala Glu Phe Arg His Asp Ser Gly Tyr Glu Val Gly Ser Gly Lys
 1               5                  10                  15
```

<210> SEQ ID NO 16
<211> LENGTH: 16
<212> TYPE: PRT
<213> ORGANISM: Artificial Sequence

```
<220> FEATURE:
<223> OTHER INFORMATION: Peptide APP1
<220> FEATURE:
<221> NAME/KEY: MOD_RES
<222> LOCATION: (16)...(16)
<223> OTHER INFORMATION: Biotinylated

<400> SEQUENCE: 16
```

Ser Glu Val Lys Met Asp Ala Glu Phe Arg His Asp Gly Ser Gly Lys
1               5                   10                  15

```
<210> SEQ ID NO 17
<211> LENGTH: 115
<212> TYPE: PRT
<213> ORGANISM: Mouse

<400> SEQUENCE: 17
```

Glu Val Lys Leu Val Glu Ser Gly Gly Gly Leu Val Gln Pro Gly Gly
1               5                   10                  15

Ser Leu Lys Leu Ser Cys Ala Val Ser Gly Phe Thr Phe Ser Asp Asn
            20                  25                  30

Gly Met Ala Trp Val Arg Gln Ala Pro Arg Lys Gly Pro Glu Trp Ile
        35                  40                  45

Ala Phe Ile Ser Asn Leu Ala Tyr Ser Ile Asp Tyr Ala Asp Thr Val
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Val Ser Gly Thr Trp Phe Ala Tyr Trp Gly Gln Gly Thr Leu Val Thr
            100                 105                 110

Val Ser Ala
        115

```
<210> SEQ ID NO 18
<211> LENGTH: 345
<212> TYPE: DNA
<213> ORGANISM: Mouse

<400> SEQUENCE: 18
```

| | | | | | |
|---|---|---|---|---|---|
| gaggtgaagc | tggtggagtc | tgggggaggc | ttagtgcagc | ctggagggtc | cctgaaactc    60 |
| tcctgtgcag | tctctggatt | cactttcagt | gacaacggaa | tggcgtgggt | tcgacaggct   120 |
| ccaaggaagg | ggcctgagtg | gatagcgttc | attagtaatt | tggcatatag | tatcgactac   180 |
| gcagacactg | tgacgggccg | attcaccatc | tctagagata | atgccaagaa | taccctgtac   240 |
| ctggaaatga | gcagtctgag | gtctgaggac | acggccatgt | actattgtgt | aagcgggacc   300 |
| tggtttgctt | actggggcca | aggactctg | gtcactgtct | ctgca |    345 |

```
<210> SEQ ID NO 19
<211> LENGTH: 112
<212> TYPE: PRT
<213> ORGANISM: Mouse

<400> SEQUENCE: 19
```

Asp Val Val Leu Thr Gln Thr Pro Leu Ser Leu Pro Val Ser Leu Gly
1               5                   10                  15

Asp Gln Ala Ser Ile Ser Cys Arg Val Ser Gln Ser Leu Leu His Ser
            20                  25                  30

Asn Gly Tyr Thr Tyr Leu His Trp Tyr Leu Gln Lys Pro Gly Gln Ser

```
            35                  40                  45
Pro Lys Leu Leu Ile Tyr Lys Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Leu Gly Val Tyr Phe Cys Ser Gln Thr
                 85                  90                  95
Arg His Val Pro Tyr Thr Phe Gly Gly Gly Thr Lys Leu Glu Ile Lys
            100                 105                 110

<210> SEQ ID NO 20
<211> LENGTH: 336
<212> TYPE: DNA
<213> ORGANISM: Mouse

<400> SEQUENCE: 20
gatgttgtgc tgacccaaac tccactctcc ctgcctgtca gtcttggaga tcaagcctcc       60
atctcttgca gagttagtca gagccttttta cacagtaatg gatacaccta tttacattgg      120
tacctgcaga agccaggcca gtctccaaag ctcctgatct acaaagtttc caaccgattt      180 tctgggtcc cagacaggtt cagtggcagt ggatcaggga cagatttcac actcaagatc      240
agcagagtgg aggctgagga tctgggagtt tatttctgct ctcaaactag acatgttccg      300
tacacgttcg gaggggggac caagctggaa ataaaa                                336

<210> SEQ ID NO 21
<211> LENGTH: 98
<212> TYPE: PRT
<213> ORGANISM: Human

<400> SEQUENCE: 21

Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Ser Tyr
                 20                  25                  30
Ser Met Asn Trp Val Arg Gln Ala Pro Gly Lys Gly Leu Glu Trp Val
             35                  40                  45
Ser Tyr Ile Ser Ser Ser Ser Thr Ile Tyr Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg

<210> SEQ ID NO 22
<211> LENGTH: 296
<212> TYPE: DNA
<213> ORGANISM: Human

<400> SEQUENCE: 22
gaggtgcagc tggtggagtc tgggggaggc ttggtacagc ctggggggtc cctgagactc       60
tcctgtgcag cctctggatt caccttcagt agctatagca tgaactgggt ccgccaggct      120
ccagggaagg ggctgagtg gtttcatac attagtagta gtagtagtac catatactac      180
gcagactctg tgaagggccg attcaccatc tccagagaca tgccaagaa ctcactgtat      240 ctgcaaatga acagcctgag agccgaggac acggctgtgt attactgtgc gagaga         296
```

```
<210> SEQ ID NO 23
<211> LENGTH: 15
<212> TYPE: PRT
<213> ORGANISM: Human

<400> SEQUENCE: 23

Tyr Phe Asp Tyr Trp Gly Gln Gly Thr Leu Val Thr Val Ser Ser
1               5                   10                  15

<210> SEQ ID NO 24
<211> LENGTH: 112
<212> TYPE: PRT
<213> ORGANISM: Human

<400> SEQUENCE: 24

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 25
<211> LENGTH: 336
<212> TYPE: DNA
<213> ORGANISM: Human

<400> SEQUENCE: 25
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttgggttc taatcgggcc     180
tccggggtcc ctgacaggtt cagtggcagt ggatcaggca cagattttac actgaaaatc     240
agcagagtgg aggctgagga tgttggggtt tattactgca tgcaagctct acaaactccg     300
tggacgttcg gccaagggac caaggtggaa atcaaa                               336

<210> SEQ ID NO 26
<211> LENGTH: 115
<212> TYPE: PRT
<213> ORGANISM: Artificial Sequence
<220> FEATURE:
<223> OTHER INFORMATION: Humanised

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Asn
            20                  25                  30

Gly Met Ala Trp Val Arg Gln Ala Pro Gly Lys Gly Leu Glu Trp Val
        35                  40                  45
```

```
Ser Phe Ile Ser Asn Leu Ala Tyr Ser Ile Asp Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Ser Gly Thr Trp Phe Ala Tyr Trp Gly Gln Gly Thr Leu Val Thr
            100                 105                 110

Val Ser Ser
        115

<210> SEQ ID NO 27
<211> LENGTH: 345
<212> TYPE: DNA
<213> ORGANISM: Human

<400> SEQUENCE: 27
gaggtgcagc tggtggagtc tgggggaggc ttggtacagc ctggggggtc cctgagactc      60
tcctgtgcag cctctggatt caccttcagt gacaacggaa tggcgtgggt ccgccaggct     120
ccagggaagg ggctggagtg ggtttcattc attagtaatt ggcatatag  tatcgactac     180 gcagacactg tgacgggccg attcaccatc tccagagaca atgccaagaa ctcactgtat     240
ctgcaaatga acagcctgag agccgaggac acggctgtgt attactgtgt cagcgggacc     300
tggtttgctt actggggcca gggcacacta gtcacagtct cctca                    345

<210> SEQ ID NO 28
<211> LENGTH: 115
<212> TYPE: PRT
<213> ORGANISM: Human

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asp Asn
            20                  25                  30

Gly Met Ala Trp Val Arg Gln Ala Pro Gly Lys Gly Leu Glu Trp Val
        35                  40                  45

Ser Phe Ile Ser Asn Leu Ala Tyr Ser Ile Asp Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Ser Gly Thr Trp Phe Ala Tyr Trp Gly Gln Gly Thr Leu Val Thr
            100                 105                 110

Val Ser Ser
        115

<210> SEQ ID NO 29
<211> LENGTH: 345
<212> TYPE: DNA
<213> ORGANISM: Human

<400> SEQUENCE: 29
gaggtgcagc tggtggagtc tgggggaggc ttggtacagc ctggggggtc cctgagactc      60
tcctgtgcag tctctggatt caccttcagt gacaacggaa tggcgtgggt ccgccaggct     120
```

```
ccagggaagg ggctggagtg ggtttcattc attagtaatt tggcatatag tatcgactac      180
gcagacactg tgacgggccg attcaccatc tccagagaca tgccaagaa ctcactgtat       240 ctgcaaatga acagcctgag agccgaggac acggctgtgt attactgtgt cagcgggacc     300
tggtttgctt actggggcca gggcacacta gtcacagtct cctca                      345
```

<210> SEQ ID NO 30
<211> LENGTH: 115
<212> TYPE: PRT
<213> ORGANISM: Human

<400> SEQUENCE: 30

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Asn
             20                  25                  30

Gly Met Ala Trp Val Arg Gln Ala Pro Gly Lys Gly Leu Glu Trp Ile
         35                  40                  45

Ser Phe Ile Ser Asn Leu Ala Tyr Ser Ile Asp Tyr Ala Asp Thr Val
     50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Ser Gly Thr Trp Phe Ala Tyr Trp Gly Gln Gly Thr Leu Val Thr
            100                 105                 110

Val Ser Ser
        115
```

<210> SEQ ID NO 31
<211> LENGTH: 345
<212> TYPE: DNA
<213> ORGANISM: Human

<400> SEQUENCE: 31

```
gaggtgcagc tggtggagtc tgggggaggc ttggtacagc ctggggggtc cctgagactc      60
tcctgtgcag cctctggatt caccttcagt gacaacggaa tggcgtgggt ccgccaggct     120
ccagggaagg ggctggagtg gatctcattc attagtaatt tggcatatag tatcgactac     180
gcagacactg tgacgggccg attcaccatc tccagagaca tgccaagaa ctcactgtat      240 ctgcaaatga acagcctgag agccgaggac acggctgtgt attactgtgt cagcgggacc    300
tggtttgctt actggggcca gggcacacta gtcacagtct cctca                    345
```

<210> SEQ ID NO 32
<211> LENGTH: 112
<212> TYPE: PRT
<213> ORGANISM: Human

<400> SEQUENCE: 32

```
Asp Ile Val Met Thr Gln Ser Pro Leu Ser Leu Pro Val Thr Pro Gly
  1               5                  10                  15

Glu Pro Ala Ser Ile Ser Cys Arg Val Ser Gln Ser Leu Leu His Ser
             20                  25                  30

Asn Gly Tyr Thr Tyr Leu His Trp Tyr Leu Gln Lys Pro Gly Gln Ser
         35                  40                  45

Pro Gln Leu Leu Ile Tyr Lys Val Ser Asn Arg Phe Ser Gly Val Pro
```

```
                50              55              60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Thr
                 85                  90                  95

Arg His Val Pro Tyr Thr Phe Gly Gly Gly Thr Lys Val Glu Ile Lys
            100                 105                 110
```

<210> SEQ ID NO 33
<211> LENGTH: 336
<212> TYPE: DNA
<213> ORGANISM: Human

<400> SEQUENCE: 33

```
gatattgtga tgactcagtc tccactctcc ctgcccgtca cccctggaga gccggcctcc      60
atctcctgca gagttagtca gagccttttta cacagtaatg gatacaccta tttacattgg    120
tacctgcaga agccaggcca gtctccacag ctcctgatct ataaagtttc caaccgattt    180
tctggggtcc ctgacaggtt cagtggcagt ggatcaggca cagatttat actgaaaatc    240
agcagagtgg aggctgagga tgttggggtt tattactgct ctcaaactag acatgttccg    300
tacacgttcg gcgagggac caaggtggaa atcaaa                                336
```

<210> SEQ ID NO 34
<211> LENGTH: 445
<212> TYPE: PRT
<213> ORGANISM: Human

<400> SEQUENCE: 34

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Asn
             20                  25                  30

Gly Met Ala Trp Val Arg Gln Ala Pro Gly Lys Gly Leu Glu Trp Val
         35                  40                  45

Ser Phe Ile Ser Asn Leu Ala Tyr Ser Ile Asp Tyr Ala Asp Thr Val
 50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Val Ser Gly Thr Trp Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
```

```
                210               215               220
Pro Pro Cys Pro Ala Pro Glu Leu Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 35
<211> LENGTH: 1335
<212> TYPE: DNA
<213> ORGANISM: Human

<400> SEQUENCE: 35
gaggtgcagc tggtggagtc tgggggaggc ttggtacagc ctgggggtc cctgagactc      60 tcctgtgcag cctctggatt caccttcagt gacaacggaa tggcgtgggt ccgccaggct    120
ccagggaagg ggctggagtg ggtttcattc attagtaatt tggcatatag tatcgactac    180
gcagacactg tgacgggccg attcaccatc tccagagaca atgccaagaa ctcactgtat    240
ctgcaaatga acagcctgag agccgaggac acggctgtgt attactgtgt cagcgggacc    300
tggtttgctt actggggcca gggcacacta gtcacagtct cctcagcctc caccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagaaagttg agcccaaatc ttgtgacaaa    660
actcacacat gcccaccgtg cccagcacct gaactcgcgg ggggcaccgtc agtcttcctc    720 ttccccccaa aacccaagga caccctcatg atctcccgga cccctgaggt cacatgcgtg    780
gtggtggacg tgagccacga agaccctgag gtcaagttca actggtacgt ggacggcgtg    840
```

```
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caagggcag   1020 ccccgagaac acaggtgta caccctgccc ccatcccggg atgagctgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaa                                                     1335
```

<210> SEQ ID NO 36
<211> LENGTH: 445
<212> TYPE: PRT
<213> ORGANISM: Human

<400> SEQUENCE: 36

```
Glu Val Gln Leu Val Glu Ser Gly Gly Gly Leu Val Gln Pro Gly Gly
  1               5                  10                  15

Ser Leu Arg Leu Ser Cys Ala Val Ser Gly Phe Thr Phe Ser Asp Asn
             20                  25                  30

Gly Met Ala Trp Val Arg Gln Ala Pro Gly Lys Gly Leu Glu Trp Val
         35                  40                  45

Ser Phe Ile Ser Asn Leu Ala Tyr Ser Ile Asp Tyr Ala Asp Thr Val
     50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Ser Gly Thr Trp Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
```

```
            275                 280                 285
Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 37
<211> LENGTH: 1335
<212> TYPE: DNA
<213> ORGANISM: Human

<400> SEQUENCE: 37
gaggtgcagc tggtggagtc tgggggaggc ttggtacagc ctgggggtc cctgagactc    60
tcctgtgcag tctctggatt caccttcagt gacaacggaa tggcgtgggt ccgccaggct   120
ccagggaagg gctgagtg gtttcattc attagtaatt ggcatatag tatcgactac      180
gcagacactg tgacgggccg attcaccatc tccagagaca atgccaagaa ctcactgtat   240
ctgcaaatga acagcctgag agccgaggac acggctgtgt attactgtgt cagcgggacc   300
tggtttgctt actggggcca gggcacacta gtcacagtct cctcagcctc caccaagggc   360
ccatcggtct tccccctggc accctcctcc aagagcacct ctgggggcac agcggccctg   420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
agcagcgtgg tgaccgtgcc ctccagcagc ttgggcaccc agacctacat ctgcaacgtg   600
aatcacaagc ccagcaacac caaggtggac aagaaagttg agcccaaatc ttgtgacaaa   660
actcacacat gcccaccgtg cccagcacct gaactcgcgg ggcaccgtc agtcttcctc    720
ttccccccaa aacccaagga caccctcatg atctcccgga cccctgaggt cacatgcgtg   780
gtggtggacg tgagccacga agaccctgag gtcaagttca actggtacgt ggacggcgtg   840
gaggtgcata atgccaagac aaagccgcgg gaggagcagt acaacagcac gtaccgtgtg   900
gtcagcgtcc tcaccgtcct gcaccaggac tggctgaatg gcaaggagta caagtgcaag   960
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
```

```
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                      1335
```

<210> SEQ ID NO 38
<211> LENGTH: 445
<212> TYPE: PRT
<213> ORGANISM: Human

<400> SEQUENCE: 38

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Asn
             20                  25                  30

Gly Met Ala Trp Val Arg Gln Ala Pro Gly Lys Gly Leu Glu Trp Ile
         35                  40                  45

Ser Phe Ile Ser Asn Leu Ala Tyr Ser Ile Asp Tyr Ala Asp Thr Val
     50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Ser Gly Thr Trp Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
```

```
              340                 345                 350
Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445
```

<210> SEQ ID NO 39
<211> LENGTH: 1335
<212> TYPE: DNA
<213> ORGANISM: Human

<400> SEQUENCE: 39

```
gaggtgcagc tggtggagtc tggggggaggc ttggtacagc ctggggggtc cctgagactc      60
tcctgtgcag cctctggatt caccttcagt gacaacggaa tggcgtgggt ccgccaggct     120
ccagggaagg ggctggagtg gatctcattc attagtaatt ggcatatag tatcgactac      180
gcagacactg tgacgggccg attcaccatc tccagagaca atgccaagaa ctcactgtat     240
ctgcaaatga acagcctgag agccgaggac acggctgtgt attactgtgt cagcgggacc     300
tggtttgctt actggggcca gggcacacta gtcacagtct cctcagcctc caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaactcgcgg gggaccgtc agtcttcctc      720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc agcccccatc gagaaaacca tctccaaagc caaagggcag    1020
ccccgagaac cacaggtgta caccctgccc ccatcccggg atgagctgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                      1335
```

<210> SEQ ID NO 40
<211> LENGTH: 219
<212> TYPE: PRT
<213> ORGANISM: Human

<400> SEQUENCE: 40

```
Asp Ile Val Met Thr Gln Ser Pro Leu Ser Leu Pro Val Thr Pro Gly
 1               5                  10                  15
Glu Pro Ala Ser Ile Ser Cys Arg Val Ser Gln Ser Leu Leu His Ser
             20                  25                  30
Asn Gly Tyr Thr Tyr Leu His Trp Tyr Leu Gln Lys Pro Gly Gln Ser
         35                  40                  45
Pro Gln Leu Leu Ile Tyr Lys Val Ser Asn Arg Phe Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Ser Gln Thr
                 85                  90                  95
Arg His Val Pro Tyr Thr Phe Gly Gly Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215
```

<210> SEQ ID NO 41
<211> LENGTH: 657
<212> TYPE: DNA
<213> ORGANISM: Human

<400> SEQUENCE: 41

```
gatattgtga tgactcagtc tccactctcc ctgcccgtca cccctggaga gccggcctcc    60
atctcctgca gagttagtca gagcctttta cacagtaatg gatacaccta tttacattgg   120
tacctgcaga agccagggca gtctccacag ctcctgatct ataaagtttc caaccgattt   180
tctggggtcc ctgacaggtt cagtggcagt ggatcaggca cagattttac actgaaaatc   240
agcagagtgg aggctgagga tgttggggtt tattactgct ctcaaactag acatgttccg   300
tacacgttcg gcggagggac caaggtggaa atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggacaa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt      657
```

<210> SEQ ID NO 42
<211> LENGTH: 1335
<212> TYPE: DNA

<213> ORGANISM: Human

<400> SEQUENCE: 42

```
gaggtgcagc tggtggagtc tgcggcgga ctggtgcagc tggcggcag cctgagactg      60
agctgtgccg tgtccggctt caccttcagc gacaacggca tggcctgggt gaggcaggcc    120
cctggcaagg gcctggagtg ggtgtccttc atcagcaacc tggcctacag catcgactac    180
gccgacaccg tgaccggcag attcaccatc agccgggaca cgccaagaa cagcctgtac     240
ctgcagatga acagcctgag agccgaggac accgccgtgt actactgtgt gagcggcacc    300
tggttcgcct actggggcca gggcaccctg gtgaccgtgt ccagcgccag caccaagggc    360
cccagcgtgt tccccctggc cccagcagc aagagcacca gcggcggcac agccgccctg     420
ggctgcctgg tgaaggacta cttccccgaa ccggtgaccg tgtcctggaa cagcggagcc    480
ctgaccagcg gcgtgcacac cttccccgcc gtgctgcaga gcagcggcct gtacagcctg    540
agcagcgtgg tgaccgtgcc agcagcagc ctgggcaccc agacctacat ctgtaacgtg     600
aaccacaagc ccagcaacac caaggtggac aagaaggtgg agcccaagag ctgtgacaag    660
acccacacct gcccccctg ccctgccccc gagctggccg agcccccag cgtgttcctg      720
ttcccccca agcctaagga cacctgatg atcagcagaa ccccgaggt gacctgtgtg       780
gtggtggatg tgagccacga ggaccctgag gtgaagttca actggtacgt ggacggcgtg    840
gaggtgcaca atgccaagac caagcccagg gaggagcagt acaacagcac ctaccgggtg    900
gtgtccgtgc tgaccgtgct gcaccaggat tggctgaacg gcaaggagta caagtgtaag    960
gtgtccaaca aggccctgcc tgcccctatc gagaaaacca tcagcaaggc caagggccag   1020
cccagagagc cccaggtgta caccctgccc ctagcagag atgagctgac caagaaccag    1080
gtgtccctga cctgcctggt gaagggcttc taccccagcg acatcgccgt ggagtgggag   1140
agcaacggcc agcccgagaa caactacaag accacccccc ctgtgctgga cagcgatggc   1200
agcttcttcc tgtacagcaa gctgaccgtg gacaagagca gatggcagca gggcaacgtg   1260
ttcagctgct ccgtgatgca cgaggccctg cacaatcact acacccagaa gagcctgagc   1320
ctgtcccctg gcaag                                                    1335
```

<210> SEQ ID NO 43
<211> LENGTH: 657
<212> TYPE: DNA
<213> ORGANISM: Human

<400> SEQUENCE: 43

```
gacatcgtga tgacccagag ccccctgagc ctgcccgtga cccctggcga gcccgccagc     60
atcagctgta gagtgagcca gagcctgctg cacagcaacg gctacaccta cctgcactgg   120
tatctgcaga gcctggcca gagccctcag ctgctgatct acaaggtgtc caaccggttc    180
agcggcgtgc ctgatagatt cagcggcagc ggctccggca ccgacttcac cctgaagatc   240
agcagagtgg aggccgagga tgtgggcgtg tactactgct cccagaccag acacgtgcct   300
tacaccttg cggcggaac aaaggtggag atcaagcgta cggtggccgc cccagcgtg     360
ttcatcttcc cccccagcga tgagcagctg aagagcggca ccgccagcgt ggtgtgtctg   420
ctgaacaact ctacccccg ggaggccaag gtgcagtgga aggtggacaa tgccctgcag    480
agcggcaaca gccaggagag cgtgaccgag caggacagca aggactccac ctacagcctg   540
agcagcaccc tgaccctgag caaggccgac tacgagaagc acaaggtgta cgcctgtgag   600
gtgacccacc agggcctgtc cagccccgtg accaagagct tcaaccgggg cgagtgc      657
```

```
<210> SEQ ID NO 44
<211> LENGTH: 16
<212> TYPE: PRT
<213> ORGANISM: Artificial Sequence
<220> FEATURE:
<223> OTHER INFORMATION: 16mer peptide containing residues 2-13 of beta
      amyloid peptide
<220> FEATURE:
<221> NAME/KEY: MOD_RES
<222> LOCATION: (16)...(0)
<223> OTHER INFORMATION: Biotinylated

<400> SEQUENCE: 44

Ala Glu Phe Arg His Asp Ser Gly Tyr Glu Val His Gly Ser Gly Lys
1               5                   10                  15
```

ANTIGEN BINDING PROTEINS

This application is a 371 of International Application No. PCT/EP2008/062652, filed Sep. 23, 2008, which claims the priority of GB Application No. 0718737.0, filed Sep. 25, 2007, which are incorporated herein in their entirety.

FIELD OF THE INVENTION

The present invention relates to methods of treating diseases or disorders affecting the eye or optic nerve characterised by elevated β-amyloid levels or β-amyloid deposits, particularly age related macular degeneration and glaucoma type diseases and β-amyloid dependent cataract formation, with antigen binding proteins that bind β-amyloid peptide and in particular human β-amyloid peptide. Other aspects of the present invention will be apparent from the description below.

BACKGROUND OF THE INVENTION

It has become increasingly apparent that the transport of β-amyloid (Aβ) between the central nervous system (CNS) and plasma plays a key role in the regulation of brain β-amyloid levels, with Aβ being efficiently transported between the CNS and CSF (cerebral spinal fluid), CSF and blood and CNS and blood (Shibata (2000); Zlokovic (2004); Deane and Zlokovic (2007)). Therefore active vaccination with Aβ peptides or passive administration of specific Aβ antibodies rapidly binds peripheral Aβ altering the dynamic equilibrium between plasma, CSF and ultimately the CNS. This principle can also be applied to other areas where barriers potentially prevent the free exchange of Aβ or uptake of antibodies themselves such as the blood retinal barrier and access to the plaque-like deposits, or drusen, formed beneath the basement membrane of the retinal pigment epithelial (RPE) cell layer and the inner layer of the Bruch's membrane (Luibl et al (2006)). It has been postulated that through binding of β-amyloid in the periphery in blood, a so-called "sink" can be established by applying a physical gradient across the barrier leading to a lowering of β-amyloid levels within the compartment and its environment leading in turn to a reduction in Aβ-associated pathology (DeMattos et al (2002)). This could provide benefit in terms of cell survival by for example preventing cytotoxic effects of certain forms of β-amyloid. On the other hand antibodies have also been shown to penetrate across the blood brain barrier and hence may also elucidate effects by entering directly into the environment of the cells affected by β-amyloid related toxicity and act by removing or neutralising β-amyloid, by preventing deposition or by altering amyloid precursor processing (Deane et al. (2005); Bard et al (2000); Rakover et al (2006))

Age-related macular degeneration (AMD) is the leading cause of blindness in the developed world. There are two major clinical presentations of AMD. Atrophic (dry) AMD is characterised by the degeneration of retinal pigment epithelial (RPE) and neuroretina. The early stages of atrophic AMD are associated with the formation of drusen, under the RPE cell layer. Early atrophic AMD can progress to an end stage disease where the RPE degenerates completely and forms sharply demarcated areas of RPE atrophy in the region of the macula: "geographic atrophy". In this form of the disease, the degeneration of RPE results in the secondary death of macular rods and cones and in these cases this leads to the severe age-related vision loss. A proportion of AMD patients develop what can either be regarded as a different form or a further complication of the disease. Approximately 10-20% of AMD patients develop choroidal neovascularisation, (CNV). When this occurs the form of the disease is known as "wet AMD" and this can be associated with some of the most severe vision loss. In wet AMD, new choroidal vessels grow through breaks in Bruch's membrane and proliferate into and under the RPE and neuroretina. In typical cases, atrophic AMD develops in the eye before the development of the wet form, however, on infrequent occasions, the neovascular form can develop in the absence of prior development of the atrophic form. In both forms of the disease, vision loss occurs due to the death of photoreceptor cells, although in wet AMD internal bleeding from the leaky vessels formed during CNV also causes vision loss. In terms of therapy for AMD there has been some progress in developing novel treatments to address some aspects of wet AMD, in particular the reduction of leaky vessel bleeding from CNV by various molecules that inhibit either VEGF, (vascular endothelial growth factor) or the VEGF receptor signalling pathway. However, currently there are no definitive means of treatment for the very prevalent atrophic form of AMD nor to prevent the progression of early dry AMD either to geographic atrophy or to wet AMD, (Petrukhin K (2007)).

There are considerable similarities between the formation of drusen in AMD and in the formation of plaques in Alzheimer's disease (AD). Drusen have been found from histo-pathological and proteomic studies to contain similar types of protein components to AD plaques. The presence of apolipoprotein E and β-amyloid, (Aβ), protein as components of drusen in atrophic AMD suggests some sharing of the pathways of AD plaque and AMD drusen formations. The Aβ found in drusen is thought to be locally derived from the RPE cells. The involvement of the ageing process and also secondary inflammatory arrest also appears to be linked in both AMD and AD. In the inflammatory process associated with AMD there is an associated rise in expression of acute-proteins such as C-reactive protein (CRP) and Aβ protein. Both of these proteins are part of the pentraxin protein class and they may both induce complement activation and the activation of pro-inflammatory cytokines. Activated complement components are also found in drusen and a number of polymorphisms in genes involved in the alternative complement pathway have been shown to be associated with the development of AMD. Many polymorphisms have been described especially in the key regulator complement factor H, (CFH), but also in Factor B, C2 and C3. The implication of such polymorphisms is that a dysfunctionally activated or regulated alternative complement pathway is associated with AMD. The activated complement components lead to the formation of a final membrane attack complex which can lyse cells and lead to the release of cytokines such as VEGF. In diseases such as AD the deposition of plaques containing Aβ protein and neurofibrillary tangles are known to activate the complement pathway so it is possible that the presence of Aβ protein in drusen has a similar effect in AMD, (Rodrigues E (2007); Johnson L V (2001); Hageman G S et al., (2001)). A recent study investigated the prevalence of AMD amongst patients with AD in the USA and found that approximately double the number of expected cases of both late stage and early stage AMD were found in AD patients, (Baumritter et al., (2007)). Conversely an earlier, prospective population-based study had identified an increased risk of developing AD in individuals with advanced AMD, (Klaver C C et al., (1999)).

Initial studies to characterise the β-amyloid present in drusen appeared to highlight some differences from the β-amyloid present in AD plaques. Some drusen were found to stain weakly with Congo red, but no drusen β-amyloid seemed to show the green birefringence of β-amyloids stained with Congo red and observed under polarized light as with AD plaque β-amyloid. Confirmation of the β-amyloid present in drusen could however be demonstrated by both crystal violet and thioflavin T staining. The conclusion from this initial work was that the data was strongly suggestive that drusen exhibits some of the characteristics of β-amyloid and contains several β-amyloid-associated proteins but that they do not contain the fibrils characteristic of true β-amyloids. However, this study was unable to detect Aβ peptide, the principal component of cerebral β-amyloid in AD, nor amyloid precursor protein, (APP) in drusen, (Mullins R F et al. (2000)). This was in contrast to an early study that had reported the reaction of drusen with monoclonal antibodies directed against Aβ peptide, (Loeffler K et al., (1995)).

Further very detailed characterisation of the β-amyloid present in drusen and the association with ageing and AMD has been performed (Johnson L V et al., (2002), Anderson D H et al., (2004)). The β-amyloid is found to be associated with a sub-structural vesicular component of drusen and this co-localizes with activated complement components, (complement C3), into so-called "amyloid vesicles" which could also be primary sites of complement activation where the β-amyloid deposition could trigger local activation of the complement cascade. β-Amyloid could therefore be an important component of the local inflammatory events that lead to RPE atrophy, drusen biogenesis and the pathogenesis of AMD. The ultra-structural organization and the histochemical staining properties of the β-amyloid-containing drusen were studied in 152 donor human eyes. The β-amyloid is found in spherical elements organised as concentric ring-like structures and these are common sub-structural components of drusen. The sub-structures are composed of a central core with one or more concentric inner rings and most of the immunoreactivity to Aβ is associated with the outer layers of densely packed spherical sub-units, where punctuate regions iC3b can also be identified. The spherical structures are found in hard drusen and range from 2-10 um in diameter and can be seen in both macular and peripheral drusen in donor eyes both with and without clinical AMD. A morphometric analysis was performed on the drusen from the 152 donor samples of which 82 had clinical evidence of AMD. Drusen load varied with age in this study. The percentage of donors with little or no drusen dropped dramatically with age and there was an increase in the percentage of donors with moderate to heavy drusen loads with age, especially in those donors over 70 years of age. For the donors with light drusen loads, the percentage of donors with evidence of Aβ assemblies was almost 50%, whereas, for those donors with moderate to heavy drusen loads the percentage with Aβ assemblies approached 100%. Around half of those donors without clinical AMD had drusen which showed evidence of Aβ assemblies, but for those donors with clinically defined AMD, around 100% possessed some drusen with the Aβ assemblies. Some drusen can be densely packed with "amyloid vesicles" and this can account for a significant proportion of their total volume. Other smaller drusen may contain only a single large vesicle which again may account for a large proportion of drusen mass. Vesicles were sometimes found in the process of budding or fusing. Aβ immunoreactivity was also found in the cytoplasm of RPE cells (Anderson D H et al., (2004)). Some RPE cells that are either displaced by or flank drusen contained structures that appear similar to the β-amyloid vesicles in drusen. The staining pattern of the Aβ derived from RPE was thought to be from degenerate RPE cells that were transitioning to the formation of mature drusen. Longitudinally, oriented fibril arrays which are characteristic of aggregated β-amyloid fibrils in the brain of AD patients could not be identified in the drusen. The structures found in drusen seemed to represent a new type of macromolecular assembly of Aβ and activated complement components. The presence of Aβ was confirmed in drusen and the expression of the amyloid precursor protein, (APP), from which it is derived was highlighted in RPE cells using a number of antibody reagents with documented binding activity in AD plaques:
  (i) Mouse anti Aβ monoclonal antibody 6E10 with epitope in amino acids 1-16, (Chemicon),
  (ii) Mouse anti Aβ monoclonal antibody 4G8 with epitope in amino acids 17-24, (Signet Laboratories, Dedham, Mass., USA),
  (iii) Mouse anti APP monoclonal antibody 22C11 with epitope outside of the β-amyloid peptide but within amino acids 66-81 of human APP N-terminus, (Chemicon),
  (iv) Goat anti APP polyclonal antibody which was raised against a peptide of amino acids 44-63 of human APP, (Chemicon).

Both of the monoclonal antibodies 6E10 and 4G8 were able to label the amyloid vesicles in drusen. The APP-specific monoclonal antibody, (22C11), showed only some particulate staining of RPE cytoplasm and not labelling of the amyloid vesicles. Although some of the 6E10 positive vesicles did also faintly stain with the APP polyclonal antibody it is likely that Aβ peptide and not APP is the positive constituent of these particles (Johnson L V et al., (2002)). Structures of a similar size and morphology to the drusen associated amyloid vesicles have been described as being reactive to the 6E10 antibody in the brains of transgenic mice expressing the human APP protein (Terai K et al., (2001)).

A study to look at the presence of Aβ in the drusen of AMD patients compared to the drusen in normal retinas found Aβ immunoreactivity in 4/9 eyes with AMD and in 0/9 normal eyes (Dentchev T, et al., (2003)). The 9 AMD retinas consisted of 3 early AMD patients, 3 with geographic atrophy and 3 with neovascular AMD and the positive samples were 2 of those with early AMD and 2 with geographic atrophy with the largest quantity of Aβ being seen at the edges of the atrophy in the eyes with geographic atrophy. It was suggested that either the Aβ containing vesicles contribute to the adjacent RPE cell death or that they result from ongoing photoreceptor or RPE dysfunction or death, but that Aβ could play a role in both the early and the later stages of AMD.

It has been suggested in some experiments that non-fibrillar Aβ intermediates and not the insoluble fibrils are responsible for the primary cytotoxic effects of Aβ, (reviewed in Anderson D H et al., (2004)). It is possible that Aβ in drusen could both contribute to the local inflammatory processes involved in AMD by triggering complement activation and by assembling into macromolecular aggregates containing cytotoxic Aβ peptide forms which could result in direct killing of RPE and/or retinal ganglion cells (Anderson D H at al., (2004)). In a further study oligomeric Aβ was detected in drusen and this did not appear to co-localize with the Aβ containing vesicles described above in drusen (Luibl et al (2006)). In this study, oligomeric Aβ reactivity was seen in all drusen but not in eyes without drusen.

In addition to the aforementioned ways in which Aβ seems to be involved in the biology of drusen and its potential roles in the aetiology of AMD, Aβ has also been reported to directly interact with VEGF and this may also play a role in the pathogenesis of both AD and AMD. VEGF has been shown to co-localize with Aβ in the plaques of brains of patients with AD. VEGF has been shown to bind very strongly to Aβ but the binding does not seem to impair VEGF cell binding or VEGF mitogenic activity at least in vitro. The role of such VEGF binding in AD is not clear (Yang S P et al., (2004)). However, VEGF plays a clear role in the pathogenesis of AMD and potential localisation of high local levels of VEGF associated with Aβ could be implicated in the generation of CNV. Activation of the alternative complement pathway and activated complement components are thought to trigger VEGF expression, but evidence has also been published that Aβ can also induce VEGF expression in human RPE cells in vitro (Yoshida T et al., (2005)). Additionally, mice disrupted for the nephrilysin gene, which encodes a peptidase that degrades Aβ, have increased deposition of Aβ under the RPE and also show increased RPE cell degeneration (Yoshida T et al., (2005)).

There are no clear animal models for the generation of all of the AMD pathology but there have been some interesting findings and parallels with the human disease shown in the ocular phenotypes of transgenic mice that carry modifications of the apolipoprotein E (apoE) gene. Association of lipid carrying apoE protein to the apoE receptor 2 has recently been shown to trigger the endocytosis of APP in neuroblastoma cells, leading to the production of Aβ (He X at al., (2007)). Transgenic mice which have had the murine ApoE gene inactivated but which instead express human Apo E variants: Apo E3 Leiden, (Kliffen M, et al., (2000)), and especially Apo E4, show, when on a high fat diet, ocular phenotypes ranging from basal laminar deposits under the RPE to drusen deposition and CNV (Malek G, et al., (2005)). The eyes of aged targeted replacement mice apoE mice expressing human Apo E4 when placed on a high fat diet developed changes which mimic the pathology of human AMD: diffuse sub-RPE deposits, drusen, thickening of Bruch's membrane, RPE atrophy, hypopigmentation and hyperpigmentation. In some cases mice develop marked CNV and there is loss of visual acuity as measured by electroretinogram (ERG). The model also demonstrates the presence of murine Aβ both associated with the CNV and with the drusen-like deposits and the presence of elevated levels of murine VEGF. The model has been used to test the hypothesis that the intravenous injection of a monoclonal antibody to β-amyloid can be used to reduce drusen load in a similar way to the reduction of Aβ containing plaques in the brains of AD models and preliminary evidence suggests that drusen load was reduced in these mice upon intravenous administration of an anti-Aβ monoclonal antibody (Bowes Rickman C (2007) & Ding, J D et al. (2008)).

In summary, this provides evidence that β-amyloid may be a key factor in AMD pathology and disease. Although the exact mechanisms that cause the production of Aβ in RPE and the exact mechanism or mechanisms by which Aβ acts to influence AMD are not completely understood, the evidence implies that clearing of Aβ by agents that bind and potentially neutralise or just remove Aβ may provide a possible route to clearing drusen in AMD, reducing complement activation in AMD, reducing RPE atrophy and potentially reducing the induction of VEGF expression in RPE and its localisation at high levels around drusen. Such therapy could therefore provide means of preventing, delaying, attenuating or reversing the loss of vision due to AMD and its progression to geographic atrophy and/or exudative AMD. This may result in decreased levels of Aβ containing drusen and/or local Aβ in the surrounding environment of the RPE and thereby interfere in both the early and later stages of AMD and treat the underlying cellular decline that causes the loss of vision.

"Glaucoma type diseases" is a nonspecific term used for a group of diseases that can lead to damage to the eye's optic nerve and result in blindness. It is a major cause of blindness in the world caused ultimately by increased intraocular pressure (IOP) and decreased visual acuity. The link between IOP and how this leads to apoptosis of the retinal ganglion cells (RGC) is not well understood. High IOP alone can induce apoptosis (Cordeiro et al (2004); Quigley et al (1995)) but in itself is not the only cause of cell death of the optic neurons. In addition it has been observed that the vision can continue to deteriorate even after the normalisation of the IOP following treatment with eye pressure lowering agents (Oliver et al (2002)).

Recently there have been reports linking the potentially cytotoxic effects of β-amyloid to apoptosis of RGCs in glaucoma (McKinnon et al (2002)). In animal models of glaucoma it has been demonstrated that caspase-3 protease is activated in RGCs which leads to abnormal processing of amyloid precursor protein (APP) by caspase-3 generating potentially toxic fragments of APP including β-amyloid (McKinnon et al (2002); Cheung et al (2004)). Amongst other cells, RGCs have been shown to express APP and this therefore appears a plausible source of β-amyloid. Both elevated levels of APP and elevated levels of β-amyloid have been implicated with activating caspase-3 although this has been observed primarily in vitro systems. It is unclear whether APP levels in the RGCs are also increased in glaucoma thus contributing to the generation of even more β-amyloid in a positive feed back mechanism. Even more recently, the involvement of β-amyloid with apoptosis of RGCs in a rat model of glaucoma has been suggested (Guo et al (2007)). Several agents targeting β-amyloid or β-amyloid production were tested and showed a reduction of retinal ganglion cell death in vivo with a possible mild enhancement effect when all three treatments were used together. The largest effect was seen by using an anti-β-amyloid antibody which almost matched the effects seen with all three agents together.

In summary this provides evidence that β-amyloid may be a key factor in the pathology of glaucoma-type diseases. Although the exact mechanisms that cause the production of β-amyloid in RGCs and the connection with IOP are not completely understood, the evidence implies that clearing of β-amyloid by agents that bind and potentially neutralise or just remove β-amyloid may provide a possible route to preventing RGC apoptosis in glaucoma and therefore provide means of delaying, attenuating or reversing the loss of vision in glaucoma. This may result in decreased levels of β-amyloid in the RGCs and surrounding environment and thereby address the underlying cellular decline that causes the loss of vision.

β-Amyloid may play a role in other ocular diseases and has been associated with the formation of supra-nuclear cataracts especially in those seen in AD patients and the components of the Aβ generation and processing pathway are present in the lens (Goldstein L E, et al., (2003); Li G, et al., (2003)). The therapeutic approaches described for intervention in AMD and glaucoma-type diseases may therefore be applicable to the prevention of Aβ dependent cataract formation.

SUMMARY OF THE INVENTION

In an embodiment of the present invention there is provided a method of treating a human patient afflicted with a disease or disorder affecting the eye or optic nerve characterised by elevated β-amyloid levels or β-amyloid deposits, which method comprises the step of administering to said patient a therapeutically effective amount of an antigen binding protein which binds β-amyloid peptide 1-12 (SEQ ID No:15) with equilibrium constant KD less than 100 pM but does not bind to β-amyloid peptide 2-13 (SEQ ID No:44), both determinations being made in a surface plasmon resonance assay utilising peptide captured on streptavidin chip.

In another embodiment of the present invention the therapeutic antigen binding protein binds β-amyloid peptide 1-12 (SEQ ID No:15) with equilibrium constant KD less than 100 pM and has an equilibrium constant KD for binding to β-amyloid peptide 2-13 (SEQ ID No:44) which is 1000-fold greater than that for peptide 1-12 (SEQ ID No:15), both determinations being made in a surface plasmon resonance assay utilising peptide captured on streptavidin chip.

In another embodiment of the present invention the therapeutic antigen binding protein binds β-amyloid peptide 1-12 (SEQ ID No:15) with equilibrium constant KD less than 100 pM and has an equilibrium constant KD for binding to β-amyloid peptide 2-13 (SEQ ID No:44) which is 10,000-fold greater than that for peptide 1-12 (SEQ ID No:15), both determinations being made in a surface plasmon resonance assay utilising peptide captured on streptavidin chip.

In one aspect the surface plasmon resonance assay utilising peptide captured on streptavidin chip is the Surface Plasmon Resonance assay described in the Example below. In another aspect the surface plasmon resonance assay utilising peptide captured on streptavidin chip is the Method A(i) described under SPR Biacore™ Analysis below.

In an alternative embodiment of the present invention the therapeutic antigen binding protein binds β-amyloid peptide 1-40 with equilibrium constant KD less than 10 nM but does not bind to β-amyloid peptide 2-13 (SEQ ID No:44), both determinations being made in the surface plasmon resonance assay described in Method B of the Examples below.

In another alternative embodiment of the present invention the therapeutic antigen binding protein binds β-amyloid peptide 1-40 with equilibrium constant KD less than 10 nM and has an equilibrium constant KD for binding to β-amyloid peptide 2-13 (SEQ ID No:44) which is 1000-fold greater than that for peptide 1-12 (SEQ ID No:15), both determinations being made in the surface plasmon resonance assay described in Method B of the Examples below.

In another alternative embodiment of the present invention the therapeutic antigen binding protein binds β-amyloid peptide 1-40 with equilibrium constant KD less than 10 nM and has an equilibrium constant KD for binding to β-amyloid peptide 2-13 (SEQ ID No:44) which is 10,000-fold greater than that for peptide 1-12 (SEQ ID No:15), both determinations being made in the surface plasmon resonance assay described in Method B of the Examples below.

In an embodiment of the present invention the therapeutic antigen binding protein is a therapeutic antibody or antigen binding fragment and/or derivative thereof which binds β-amyloid peptide and which comprises the following CDRs:

```
CDRH1:    DNGMA                (SEQ ID No: 1)
CDRH2:    FISNLAYSIDYADTVTG    (SEQ ID No: 2)
CDRH3:    GTWFAY               (SEQ ID No: 3)
``` within a human heavy chain variable region originating from the VH3 gene family and:

```
CDRL1:    RVSQSLLHSNGYTYLH     (SEQ ID No: 4)
CDRL2:    KVSNRFS              (SEQ ID No: 5)
CDRL3:    SQTRHVPYT            (SEQ ID No: 6)
``` within a human light chain variable region originating from the amino acid sequence disclosed in GenPept entry CAA51135 (SEQ ID No:24).

Throughout this specification, the terms "CDR", "CDRL1", "CDRL2", "CDRL3", "CDRH1", "CDRH2", "CDRH3" follow the Kabat numbering system as set forth in Kabat et al; Sequences of proteins of *Immunological Interest* NIH, 1987. Therefore the following defines the CDRs according to the invention:

| CDR:   | Residues |
|--------|----------|
| CDRH1: | 31-35B   |
| CDRH2: | 50-65    |
| CDRH3: | 95-102   |
| CDRL1: | 24-34    |
| CDRL2: | 50-56    |
| CDRL3: | 89-97    |

The VH3 gene family and related immunoglobulin gene nomenclature is described in Matsuda et al (Journal of Experimental Medicine, 188:2151-2162, 1998) and Lefranc & Lefranc (The Immunoglobulin Factsbook. 2001. Academic Press: London).

In a particular embodiment, the human heavy chain variable region originates from:
 A V gene selected from the following subset of VH3 family members: VHβ-48, VH3-21, VH3-11, VH3-7, VH3-13, VH3-74, VH3-64, VH3-23, VH3-38, VH3-53, VH3-66, VH3-20, VH3-9 & VH3-43
 A V gene selected from the following subset of VH3 family members: VH3-48, VH3-21 & VH3-11
 The VH3-48 gene
or an allele thereof.

The sequence in Genbank entry M99675 is an allele of the VH3-48 gene. M99675 is a Genbank nucleotide sequence of a genomic piece of DNA including the two exons that constitute the human heavy chain gene VH3-48 (SEQ ID No:22) and encode the variable region amino acid sequence given in SEQ ID No:21. In a particular aspect the human acceptor heavy chain framework is derived from M99675.

In order to construct a complete V-region a framework 4 has to be added to the germline encoded V-gene M99675. Suitable framework 4 sequences include that encoded by the human JH4 minigene (Kabat):

```
    YFDYWGQGTLVTVSS       (SEQ ID No: 23)
``` of which the initial four residues fall within the CDR3 region which is replaced by the incoming CDR from the donor antibody.

The skilled person appreciates that a germline V gene and a J gene do not include coding sequence for the entirety of heavy chain CDR3. However, in the antibodies of the invention, the CDR3 sequence is provided by the donor immunoglobulin. Accordingly, the combination of a VH gene such as VH3-48, a JH minigene such as JH4, and a set of heavy chain CDRs, such as SEQ ID No:1, SEQ ID No:2 and SEQ ID No:3 (assembled in a manner so as to mimic a mature, fully rearranged heavy chain variable region) is sufficient to define a heavy chain variable region of the invention such as that represented in SEQ ID No:26, 28, 30.

The variable region encoded by Genpept ID CAA51134 has the amino acid sequence given in SEQ ID No:24.

The light chain variable region framework sequence known by the GenPept ID CAA51134 is the deduced amino acid sequence of a fully rearranged light chain variable region and is identical to another amino acid sequence with the same frameworks in the database: Genpept accession number S40356, and is described in Klein, R., et al., Eur. J. Immunol. 23 (12), 3248-3262 (1993). The DNA coding sequence for CAA51134, accessible as Genbank Accesion No X72467, is given as SEQ ID No: 25.

In a particular embodiment of the invention the human acceptor heavy chain framework is derived from M99675 and the JH4 minigene and the human acceptor light chain framework is derived from CAA51135, optionally containing one or more, such as one to four, more particularly one to three, substitutions of amino acid residues based on the corresponding residues found in the donor $V_H$ domain having the sequence: SEQ ID No:17 and $V_L$ domain having the sequence: SEQ ID No: 19 that maintain all or substantially all of the binding affinity of the donor antibody for β-amyloid peptide.

By 'substantially all of the binding affinity' is meant that the therapeutic antibody has at most a ten-fold reduction in binding affinity compared to the donor antibody.

In a more particular embodiment the human acceptor heavy chain framework derived from M99675 and JH4 has one to four amino acid residue substitutions selected from positions 24, 48, 93 and/or 94 (Kabat numbering).

In a more particular embodiment of the invention the human acceptor heavy chain framework derived from M99675 and JH4 comprises the following residues (or a conservative substitute thereof):

| Position | Residue |
|---|---|
| (i) | |
| 93 | V |
| 94 | S |
| or | |
| (ii) | |
| 24 | V |
| 93 | V |
| 94 | S |
| or | |
| (iii) | |
| 48 | I |
| 93 | V |
| 94 | S |

In one embodiment of the invention the therapeutic antibody comprises a $V_H$ chain having the sequence set forth in SEQ ID No:26, 28 or 30 and a $V_L$ domain having the sequence set forth in SEQ ID No:32.

In another embodiment of the invention the therapeutic antibody comprises a heavy chain having the sequence set forth in SEQ ID No:34, 36 or 38 and a light chain having the sequence set forth in SEQ ID No:40.

In another embodiment of the invention the therapeutic antigen binding protein competes with an antibody comprising a heavy chain having the sequence set forth in SEQ ID No:34, 36 or 38 and a light chain having the sequence set forth in set forth in SEQ ID No:40 for binding to β-amyloid in an ELISA assay.

A person skilled in the art appreciates that in order for an antigen binding protein (antigen binding protein A) to compete with an antibody comprising a heavy chain having the sequence set forth in SEQ ID No:34, 36 or 38 and a light chain having the sequence set forth in SEQ ID No:40 (antibody B) for a specific binding site (β-amyloid), antigen binding protein A must be present in a sufficient amount to have an effect in said assay. In a particular embodiment, antigen binding protein A and antibody B are present in equimolar amounts. In another embodiment, the presence of antigen binding protein A reduces the binding of antibody B to β-amyloid in an ELISA assay by more than 5%, 10%, 20%, 30%, 40% or 50%. In another embodiment β-amyloid is bound to an immunoassay plate in an ELISA assay. In another embodiment antigen binding protein A reduces the binding of antibody B to plate bound β-amyloid, whereas a non-β-amyloid-specific control does not.

In a further embodiment of the invention the antigen binding protein is a therapeutic antibody that comprises heavy and light chains comprising polypeptides which are at least 90%, 95%, 96%, 97%, 98% or 99% identical to the amino acid sequences of SEQ ID No:34, 36 or 38, and SEQ ID No:40, respectively, wherein said antibody binds β-amyloid.

In another embodiment of the invention, the therapeutic antigen binding protein is administered in combination with an inhibitor of the complement pathway, especially the alternative complement pathway, for example, but not excluding other anti-complement approaches: complement factor H (CFH) or fragments thereof, soluble Complement Receptor 1, (sCR1) or fragments thereof, soluble membrane co-factor protein (MCP) and fragments thereof, soluble decay accelerating factor (DAF) and fragments thereof. In this context, a complement pathway inhibitor is a molecule that acts to negatively regulate the activity of a complement pathway, especially the alternative complement pathway.

In a further embodiment of the invention, the therapeutic antigen binding protein is administered in combination with an inhibitor of a complement pathway activator, especially an inhibitor of an alternative complement pathway activator, for example, but not excluding other inhibitory approaches or other complement pathway targets: an antibody or antibody fragment, for example a domain antibody, to neutralise complement factor D or complement factor B activity. The β-residue peptide inhibitor of complement component C3, compstatin, and the anti-C5a complement component antibody, pexelizumab, are also considered to be inhibitors of complement pathway activators within the context of the invention. In general, an inhibitor of a complement pathway activator is an agent that inhibits or antagonises, to some extent, a biological activity of a given complement activator such that the effect would be to negatively regulate the activity of a complement pathway, especially the alternative complement pathway.

Complement—targeted therapeutic approaches have been recently reviewed (Ricklin, D. & Lambris, J., (2007)) and the anti-complement pathway approaches described therein are considered to be covered in these embodiments in a combination approach.

The complement pathway inhibitor, or the inhibitor of a complement pathway activator, may be administered simultaneously with the therapeutic antigen binding protein of the invention, or sequentially, separately or in a staggered manner.

A pharmaceutical composition comprising a therapeutic antigen binding protein as defined herein and a complement pathway inhibitor or an inhibitor of a complement pathway activator, is also provided.

A bispecific antibody or bispecific fragment thereof having a first specificity towards β-amyloid and a second specificity towards an activator of the complement pathway, is also provided.

A therapeutic antigen binding protein as defined herein for use in treating a disease or disorder affecting the eye or optic nerve characterised by elevated β-amyloid levels or β-amyloid deposits, is also provided.

Use of a therapeutic antigen binding protein as defined herein in the manufacture of a medicament for the treatment of a disease or disorder affecting the eye or optic nerve characterised by elevated β-amyloid levels or β-amyloid deposits, is also provided.

A process for the manufacture of a therapeutic antigen binding protein comprising expressing a polynucleotide encoding the antibody in a host cell, is also provided.

In one embodiment of the invention, there is provided a polynucleotide encoding a therapeutic antibody heavy chain comprising a $V_H$ chain having the sequence set forth in SEQ ID No:26, 28 or 30.

In another embodiment of the invention, there is provided a polynucleotide encoding a therapeutic antibody light chain comprising a $V_L$ domain having the sequence set forth in SEQ ID No:32.

In another embodiment of the invention, a polynucleotide encoding a therapeutic antibody heavy chain having the sequence set forth in SEQ ID No:34, 36 or 38, is provided.

In another embodiment of the invention, a polynucleotide encoding a therapeutic antibody light chain having the sequence set forth in SEQ ID No:40, is provided.

In another embodiment of the invention, there is provided a polynucleotide encoding a therapeutic antibody heavy chain comprising the sequence set forth in SEQ ID No:35, 37, 39 or 42.

In another embodiment of the invention, there is provided a polynucleotide encoding a therapeutic antibody light chain comprising the sequence set forth in SEQ ID No:41 or 43.

In a particular embodiment, the therapeutic antibody essentially lacks the functions of a) activation of complement by the classical pathway; and b) mediating antibody-dependent cellular cytotoxicity.

DETAILED DESCRIPTION OF THE INVENTION

1. Antigen Binding Proteins
1.1 Intact Antibodies

The antigen binding proteins of the present invention may be "intact antibodies". An antigen binding protein of the invention includes a therapeutic antibody which is an antibody or antigen binding fragment and/or derivative thereof. Intact antibodies are usually heteromultimeric glycoproteins comprising at least two heavy and two light chains. Aside from IgM, intact antibodies are heterotetrameric glycoproteins of approximately 150 KDa, composed of two identical light (L) chains and two identical heavy (H) chains. Typically, each light chain is linked to a heavy chain by one covalent disulfide bond while the number of disulfide linkages between the heavy chains of different immunoglobulin isotypes varies. Each heavy and light chain also has intrachain disulfide bridges. Each heavy chain has at one end a variable domain ($V_H$) followed by a number of constant regions. Each light chain has a variable domain ($V_L$) and a constant region at its other end; the constant region of the light chain is aligned with the first constant region of the heavy chain and the light chain variable domain is aligned with the variable domain of the heavy chain. The light chains of antibodies from most vertebrate species can be assigned to one of two types called Kappa and Lambda based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b. The variable domain of the antibody confers binding specificity upon the antibody with certain regions displaying particular variability called complementarity determining regions (CDRs). The more conserved portions of the variable region are called framework regions (FR). The variable domains of intact heavy and light chains each comprise four FR connected by three CDRs. The CDRs in each chain are held together in close proximity by the FR regions and with the CDRs from the other chain contribute to the formation of the antigen binding site of antibodies. The constant regions are not directly involved in the binding of the antibody to the antigen but exhibit various effector functions such as participation in antibody dependent cell-mediated cytotoxicity (ADCC), phagocytosis via binding to Fcγ receptor, half-life/clearance rate via neonatal Fc receptor (FcRn) and complement dependent cytotoxicity via the C1q component of the complement cascade. The human IgG2 constant region lacks the ability to activate complement by the classical pathway or to mediate antibody-dependent cellular cytotoxicity. The IgG4 constant region lacks the ability to activate complement by the classical pathway and mediates antibody-dependent cellular cytotoxicity only weakly. Antibodies essentially lacking these effector functions may be termed 'non-lytic' antibodies.

1.1.1 Human Antibodies

The antigen binding proteins of the present invention may be human antibodies. Human antibodies may be produced by a number of methods known to those of skill in the art. Human antibodies can be made by the hybridoma method using human myeloma or mouse-human heteromyeloma cells lines see Kozbor J. Immunol 133, 3001, (1984) and Brodeur, Monoclonal Antibody Production Techniques and Applications, pp 51-63 (Marcel Dekker Inc, 1987). Alternative methods include the use of phage libraries or transgenic mice both of which utilize human V region repertoires (see Winter G, (1994), Annu. Rev. Immunol 12, 433-455, Green L L (1999), J. Immunol. methods 231, 11-23).

Several strains of transgenic mice are now available wherein their mouse immunoglobulin loci has been replaced with human immunoglobulin gene segments (see Tomizuka K, (2000) PNAS 97, 722-727; Fishwild D. M (1996) Nature Biotechnol. 14, 845-851, Mendez M J, 1997, Nature Genetics, 15, 146-156). Upon antigen challenge such mice are capable of producing a repertoire of human antibodies from which antibodies of interest can be selected.

Of particular note is the Trimera T M system (see Eren R et al, (1998) Immunology 93:154-161) where human lymphocytes are transplanted into irradiated mice, the Selected Lymphocyte Antibody System (SLAM, see Babcook at al, PNAS (1996) 93:7843-7848) where human (or other species) lymphocytes are effectively put through a massive pooled in vitro antibody generation procedure followed by deconvulated, limiting dilution and selection procedure and the Xenomouse II™ (Abgenix Inc). An alternative approach is available from Morphotek Inc using the Morphodoma™ technology.

Phage display technology can be used to produce human antibodies (and fragments thereof), see McCafferty; Nature, 348, 552-553 (1990) and Griffiths A D et al (1994) EMBO 13:3245-3260. According to this technique antibody V domain genes are cloned in frame into either a major or minor coat of protein gene of a filamentous bacteriophage such as M13 or fd and displayed (usually with the aid of a helper phage) as functional antibody fragments on the surface of the phage particle. Selections based on the functional properties of the antibody result in selection of the gene encoding the antibody exhibiting those properties. The phage display technique can be used to select antigen specific antibodies from libraries made from human B cells taken from individuals afflicted with a disease or disorder described above or alternatively from unimmunized human donors (see Marks; J. Mol. Bio. 222, 581-597, 1991). Where an intact human antibody is desired comprising a Fc domain it is necessary to reclone the phage displayed derived fragment into a mammalian expression vectors comprising the desired constant regions and establishing stable expressing cell lines.

The technique of affinity maturation (Marks; Bio/technol 10, 779-783 (1992)) may be used to improve binding affinity wherein the affinity of the primary human antibody is improved by sequentially replacing the H and L chain V regions with naturally occurring variants and selecting on the basis of improved binding affinities. Variants of this technique such as "epitope imprinting" are now also available see WO 93/06213. See also Waterhouse; Nucl. Acids Res 21, 2265-2266 (1993).

1.1.2 Chimaeric and Humanised Antibodies

The antigen binding proteins of the present invention may be "chimeric" or "humanized" antibodies. The use of intact non-human antibodies in the treatment of human diseases or disorders carries with it the now well established problems of potential immunogenicity especially upon repeated administration of the antibody that is the immune system of the patient may recognise the non-human intact antibody as non-self and mount a neutralising response. In addition to developing fully human antibodies (see above) various techniques have been developed over the years to overcome these problems and generally involve reducing the composition of non-human amino acid sequences in the intact therapeutic antibody whilst retaining the relative ease in obtaining non-human antibodies from an immunised animal e.g. mouse, rat or rabbit. Broadly two approaches have been used to achieve this. The first are chimaeric antibodies, which generally comprise a non-human (e.g. rodent such as mouse) variable domain fused to a human constant region. Because the antigen-binding site of an antibody is localised within the variable regions the chimaeric antibody retains its binding affinity for the antigen but acquires the effector functions of the human constant region and are therefore able to perform effector functions such as described supra. Chimaeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the H and L chain variable regions of the therapeutic antibody useful in the invention, e.g. DNA of SEQ.ID.NO 18 and 20 described supra). Hybridoma cells serve as a typical source of such DNA. Once isolated, the DNA is placed into expression vectors which are then transfected into host cells such as E. Coli, COS cells, CHO cells, PerC6 cells or myeloma cells that do not otherwise produce immunoglobulin protein to obtain synthesis of the antibody. The DNA may be modified by substituting the coding sequence for human L and H chains for the corresponding non-human (e.g. murine) H and L constant regions see e.g. Morrison; PNAS 81, 6851 (1984). Thus another embodiment of the invention the therapeutic antibody is a chimaeric antibody comprising a $V_H$ domain having the sequence: SEQ ID No:17 and a $V_L$ domain having the sequence: SEQ ID No: 19 fused to a human constant region (which maybe of a IgG isotype e.g. IgG1).

The second approach involves the generation of humanised antibodies wherein the non-human content of the antibody is reduced by humanizing the variable regions. Two techniques for humanisation have gained popularity. The first is humanisation by CDR grafting. CDRs build loops close to the antibody's N-terminus where they form a surface mounted in a scaffold provided by the framework regions. Antigen-binding specificity of the antibody is mainly defined by the topography and by the chemical characteristics of its CDR surface. These features are in turn determined by the conformation of the individual CDRs, by the relative disposition of the CDRs, and by the nature and disposition of the side chains of the residues comprising the CDRs. A large decrease in immunogenicity can be achieved by grafting only the CDRs of a non-human (e.g. murine) antibodies ("donor" antibodies) onto a suitable human framework ("acceptor framework") and constant regions (see Jones et al (1986) Nature 321, 522-525 and Verhoeyen M et al (1988) Science 239, 1534-1536). However, CDR grafting per se may not result in the complete retention of antigen-binding properties and it is frequently found that some framework residues of the donor antibody need to be preserved (sometimes referred to as "backmutations") in the humanised molecule if significant antigen-binding affinity is to be recovered (see Queen C et al (1989) PNAS 86, 10, 029-10,033, Co, M et al (1991) Nature 351, 501-502). In this case, human V regions showing the greatest sequence homology (typically 60% or greater) to the non-human donor antibody maybe chosen from a database in order to provide the human framework (FR). The selection of human FRs can be made either from human consensus or individual human antibodies. Where necessary key residues from the donor antibody are substituted into the human acceptor framework to preserve CDR conformations. Computer modelling of the antibody maybe used to help identify such structurally important residues, see WO99/48523.

Alternatively, humanisation maybe achieved by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan E. A. et al; (1991) Mol. Immunol. 28, 489-498 and Pedersen J. T. et al (1994) J. Mol. Biol. 235; 959-973). Therefore it is possible to reduce the immunogenicity of a non-human Fv by replacing exposed residues in its framework regions that differ from those usually found in human antibodies. Because protein antigenicity can be correlated with surface accessibility, replacement of the surface residues may be sufficient to render the mouse variable region "invisible" to the human immune system (see also Mark G. E. et al (1994) in *Handbook of Experimental Pharmacology vol.* 113: *The pharmacology of monoclonal Antibodies*, Springer-Verlag, pp 105-134). This procedure of humanisation is referred to as "veneering" because only the surface of the antibody is altered, the supporting residues remain undisturbed. Further alternative approaches include that set out in WO04/006955 and the procedure of Humaneering™ (Kalobios) which makes use of bacterial expression systems and produces antibodies that are close to human germline in sequence (Alfenito-M Advancing Protein Therapeutics January 2007, San Diego, Calif.).

It will be apparent to those skilled in the art that the term "derived" is intended to define not only the source in the sense of it being the physical origin for the material but also to define material which is structurally identical to the material but which does not originate from the reference source. Thus "residues found in the donor antibody" need not necessarily have been purified from the donor antibody.

It is well recognised in the art that certain amino acid substitutions are regarded as being "conservative". Amino acids are divided into groups based on common side-chain properties and substitutions within groups that maintain all or substantially all of the binding affinity of the therapeutic antibody useful in the invention are regarded as conservative substitutions, see the following Table 1:

TABLE 1

| Side chain | Members |
| --- | --- |
| Hydrophobic | met, ala, val, leu, ile |
| neutral hydrophilic | cys, ser, thr |
| Acidic | asp, glu |
| Basic | asn, gln, his, lys, arg |
| residues that influence chain orientation | gly, pro |
| aromatic | trp, tyr, phe |

1.1.3 Multi- and Bispecific Antibodies

The antigen binding proteins of the present invention may be multi-specific i.e. they may bind more than one antigen. In a particular embodiment, the antigen binding protein is a bispecific antibody. A bispecific antibody is an antibody derivative having binding specificities for at least two different epitopes and is also useful in this invention. Methods of making such antibodies are known in the art. Traditionally, the recombinant production of bispecific antibodies is based on the coexpression of two immunoglobulin H chain-L chain pairs, where the two H chains have different binding specificities see Millstein et al, Nature 305 537-539 (1983), WO93/08829 and Traunecker et al EMBO, 10, 1991, 3655-3659. Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions. It is preferred to have the CH1 region containing the site necessary for light chain binding present in at least one of the fusions. DNA encoding these fusions, and if desired the L chain are inserted into separate expression vectors and are then cotransfected into a suitable host organism. It is possible though to insert the coding sequences for two or all three chains into one expression vector. In one preferred approach, the bispecific antibody is composed of a H chain with a first binding specificity in one arm and a H-L chain pair, providing a second binding specificity in the other arm, see WO94/04690. See also Suresh et al Methods in Enzymology 121, 210, 1986.

Delivery of therapeutic proteins to the brain has been hampered by the presence of the blood brain barrier (BBB) and there is a similar blood retinal barrier between the eye and the bloodstream. Where it is desired to deliver a therapeutic antibody by the method of the invention across a biological barrier such as the BBB various strategies have been proposed to enhance such delivery where needed and similar strategies may be applicable to allow crossing of the blood retinal barrier.

In order to obtain required nutrients and factors from the blood, the BBB possesses some specific receptors, which transport compounds from the circulating blood to the brain. Studies have indicated that some compounds like insulin (see Duffy K R et al (1989) Brain Res. 420:32-38), transferin (see Fishman J B et al (1987) J. Neurosci 18:299-304) and insulin like growth factors 1 and 2 (see Pardridge W M (1986) Endocrine Rev. 7:314-330 and Duffy K R et al (1986) Metabolism 37:136-140) traverse the BBB via receptor-mediated transcytosis. Receptors for these molecules thus provide a potential means for therapeutic antibodies useful in the invention to access the brain using so—called "vectored" antibodies (see Pardridge W M (1999) Advanced Drug Delivery Review 36:299-321). For example, an antibody to transferrin receptor has been shown to be dynamically transported into the brain parenchyma (see Friden P M et al (1991) PNAS 88:4771-4775 and Friden P M et al (1993) Science 259:373-377). Thus one potential approach is to produce a bispecific antibody or bispecific fragment such as described supra wherein a first specificity is towards β-amyloid and a second specificity towards a transport receptor located at the BBB e.g. a second specificity towards the transferrin transport receptor.

Other bispecific antibodies envisaged by the present invention include a bispecific antibody or bispecific fragment thereof having a first specificity towards β-amyloid and a second specificity towards an activator of the complement pathway with the aim to inhibit its activity, for example, but not excluding others: a complement factor, such as complement factor D.

Multi-specific antigen binding proteins of the invention include proteins having a first specificity towards β-amyloid, a second specificity towards a transport receptor located at the BBB and a third specificity towards an activator of the complement pathway.

1.2 Antibody Fragments

In certain embodiments of the invention the therapeutic antibody is an antigen binding fragment. Such fragments may be functional antigen binding fragments of intact and/or humanised and/or chimaeric antibodies such as Fab, Fd, Fab', F(ab')$_2$, Fv, ScFv fragments, and immunoglobulin single variable domains of the antibodies described supra. Fragments lacking the constant region lack the ability to activate complement by the classical pathway or to mediate antibody-dependent cellular cytotoxicity. Traditionally such fragments are produced by the proteolytic digestion of intact antibodies by e.g. papain digestion (see for example, WO 94/29348) but may be produced directly from recombinantly transformed host cells. For the production of ScFv, see Bird et al; (1988) Science, 242, 423-426. In addition, antibody fragments may be produced using a variety of engineering techniques as described below.

Fv fragments appear to have lower interaction energy of their two chains than Fab fragments. To stablise the association of the $V_H$ and $V_L$ domains, they have been linked with peptides (Bird et al, (1988) Science 242, 423-426, Huston et al., PNAS, 85, 5879-5883), disulphide bridges (Glockshuber et al, (1990) Biochemistry, 29, 1362-1367) and "knob in hole" mutations (Zhu et al (1997), Protein Sci., 6, 781-788). ScFv fragments can be produced by methods well known to those skilled in the art see Whitlow et al (1991) Methods companion Methods Enzymol, 2, 97-105 and Huston et al (1993) Int. Rev. Immunol 10, 195-217. ScFv may be produced in bacterial cells such as E. Coli but are more typically produced in eukaryotic cells. One disadvantage of ScFv is the monovalency of the product, which precludes an increased avidity due to polyvalent binding, and their short half-life. Attempts to overcome these problems include bivalent (ScFv')$_2$ produced from ScFV containing an additional C terminal cysteine by chemical coupling (Adams et al. (1993) Can. Res 53, 4026-4034 and McCartney et al (1995) Protein Eng. 8, 301-314) or by spontaneous site-specific dimerization of ScFv containing an unpaired C terminal cysteine residue (see Kipriyanov et al (1995) Cell. Biophys 26, 187-204). Alternatively, ScFv can be forced to form multimers by shortening the peptide linker to between 3 to 12 residues to form "diabodies", see Holliger et al PNAS (1993), 90, 6444-6448. Reducing the linker still further can result in ScFV trimers ("triabodies", see Kortt et al (1997) Protein Eng, 10, 423-433)

and tetramers ("tetrabodies", see Le Gall et al (1999) FEBS Lett, 453, 164-168). Construction of bivalent ScFV molecules can also be achieved by genetic fusion with protein dimerizing motifs to form "miniantibodies" (see Pack et al (1992) Biochemistry 31, 1579-1584) and "minibodies" (see Hu et al (1996), Cancer Res. 56, 3055-3061). ScFv-Sc-Fv tandems ((ScFV)$_2$) may also be produced by linking two ScFv units by a third peptide linker, see Kurucz et al (1995) J. Immol. 154, 4576-4582. Bispecific diabodies can be produced through the noncovalent association of two single chain fusion products consisting of $V_H$ domain from one antibody connected by a short linker to the $V_L$ domain of another antibody, see Kipriyanov et al (1998), Int. J. Can 77, 763-772. The stability of such bispecific diabodies can be enhanced by the introduction of disulphide bridges or "knob in hole" mutations as described supra or by the formation of single chain diabodies (ScDb) wherein two hybrid ScFv fragments are connected through a peptide linker see Kontermann et al (1999) J. Immunol. Methods 226 179-188. Tetravalent bispecific molecules are available by e.g. fusing a ScFv fragment to the CH3 domain of an IgG molecule or to a Fab fragment through the hinge region see Coloma et al (1997) Nature Biotechnol. 15, 159-163. Alternatively, tetravalent bispecific molecules have been created by the fusion of bispecific single chain diabodies (see Alt et al, (1999) FEBS Lett 454, 90-94. Smaller tetravalent bispecific molecules can also be formed by the dimerization of either ScFv-ScFv tandems with a linker containing a helix-loop-helix motif (DiBi miniantibodies, see Muller et al (1998) FEBS Lett 432, 45-49) or a single chain molecule comprising four antibody variable domains ($V_H$ and $V_L$) in an orientation preventing intramolecular pairing (tandem diabody, see Kipriyanov et al, (1999) J. Mol. Biol. 293, 41-56). Bispecific F(ab')2 fragments can be created by chemical coupling of Fab' fragments or by heterodimerization through leucine zippers (see Shalaby et al, (1992) J. Exp. Med. 175, 217-225 and Kostelny et al (1992), J. Immunol. 148, 1547-1553). Also available are isolated $V_H$ and $V_L$ domains, see U.S. Pat. No. 6,248,516; U.S. Pat. No. 6,291,158; U.S. Pat. No. 6,172,197.

The phrase "immunoglobulin single variable domain" refers to an antibody variable domain ($V_H$, $V_{HH}$, $V_L$) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004, nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanised according to standard techniques available in the art, and such domains are still considered to be "domain antibodies" according to the invention. As used herein "$V_H$ includes camelid $V_{HH}$ domains.

1.3 Heteroconjugate Antibodies

Heteroconjugate antibodies are derivatives which are also useful in the present invention. Heteroconjugate antibodies are composed of two covalently joined antibodies formed using any convenient cross-linking methods. See U.S. Pat. No. 4,676,980.

1.4 Other Modifications.

The interaction between the Fc region of an antibody and various Fc receptors (FcγR) is believed to mediate the effector functions of the antibody which include antibody-dependent cellular cytotoxicity (ADCC), fixation of complement, phagocytosis and half-life/clearance of the antibody. Various modifications to the Fc region of therapeutic antibodies may be carried out depending on the desired effector property. In particular, human constant regions which essentially lack the functions of a) activation of complement by the classical pathway; and b) mediating antibody-dependent cellular cytotoxicity include the IgG4 constant region, the IgG2 constant region and IgG1 constant regions containing specific mutations as for example mutations at positions 234, 235, 236, 237, 297, 318, 320 and/or 322 disclosed in EP0307434 (WO8807089), EP 0629 240 (WO 9317105) and WO 2004/014953. Mutations at residues 235 or 237 within the CH2 domain of the heavy chain constant region (Kabat numbering; EU Index system) have separately been described to reduce binding to FcγRI, FcγRII and FcγRIII binding and therefore reduce antibody-dependent cellular cytotoxicity (ADCC) (Duncan et al. Nature 1988, 332; 563-564; Lund et al. J. Immunol. 1991, 147; 2657-2662; Chappel et al. PNAS 1991, 88; 9036-9040; Burton and Woof, Adv. Immunol. 1992, 51; 1-84; Morgan et al., Immunology 1995, 86; 319-324; Hezareh et al., J. Virol. 2001, 75 (24); 12161-12168). Further, some reports have also described involvement of some of these residues in recruiting or mediating complement dependent cytotoxicity (CDC) (Morgan et al., 1995; Xu et al., Cell. Immunol. 2000; 200:16-26; Hezareh et al., J. Virol. 2001, 75 (24); 12161-12168). Residues 235 and 237 have therefore both been mutated to alanine residues (Brett et al. Immunology 1997, 91; 346-353; Bartholomew et al. Immunology 1995, 85; 41-48; and WO9958679) to reduce both complement mediated and FcγR-mediated effects. Antibodies comprising these constant regions may be termed 'non-lytic' antibodies.

One may incorporate a salvage receptor binding epitope into the antibody to increase serum half life see U.S. Pat. No. 5,739,277.

There are five currently recognised human Fcγ receptors, FcγR(I), FcγRIIa, FcγRIIb, FcγRIIIa and neonatal FcRn. Shields et al, (2001) J. Biol. Chem 276, 6591-6604 demonstrated that a common set of IgG1 residues is involved in binding all FcγRs, while FcγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgG1 residues for binding, FcγRII and FcγRIII interact with distinct residues in addition to the common set. Alteration of some residues reduced binding only to FcγRII (e.g. Arg-292) or FcγRIII (e.g. Glu-293). Some variants showed improved binding to FcγRII or FcγRIII but did not affect binding to the other receptor (e.g. Ser-267Ala improved binding to FcγRII but binding to FcγRIII was unaffected). Other variants exhibited improved binding to FcγRII or FcγRIII with reduction in binding to the other receptor (e.g. Ser-298Ala improved binding to FcγRIII and reduced binding to FcγRII). For FcγRIIIa, the best binding IgG1 variants had combined alanine substitutions at Ser-298, Glu-333 and Lys-334. The neonatal FcRn receptor is believed to be involved in protecting IgG molecules from degradation and thus enhancing serum half life and the transcytosis across tissues (see Junghans R. P (1997) Immunol. Res 16. 29-57 and Ghetie et al (2000) Annu. Rev. Immunol. 18, 739-766). Human IgG1 residues determined to interact directly with human FcRn includes Ile253, Ser254, Lys288, Thr307, Gln311, Asn434 and His435.

The therapeutic antibody useful in the invention may incorporate any of the above constant region modifications.

In a particular embodiment, the therapeutic antibody useful in the invention essentially lacks the functions of a) activation of complement by the classical pathway; and b) mediating antibody-dependent cellular cytotoxicity. In a more particular embodiment, the therapeutic antibodies useful in the invention may have any one (or more) of the residue changes detailed above to modify half-life/clearance and/or effector functions such as ADCC and/or complement dependent cytotoxicity and/or complement lysis.

In a further embodiment of the present invention the therapeutic antibody has a constant region of isotype human IgG1 with alanine (or other disrupting) substitutions at positions 235 (e.g. L235A) and 237 (e.g. G237A) (numbering according to the EU scheme outlined in Kabat).

Other embodiments of the invention utilise glycosylation variants of the therapeutic antibodies. Glycosylation of antibodies at conserved positions in their constant regions is known to have a profound effect on antibody function, particularly effector functioning such as those described above, see for example, Boyd et al (1996), Mol. Immunol. 32, 1311-1318. Glycosylation variants of the therapeutic antibodies wherein one or more carbohydrate moiety is added, substituted, deleted or modified are contemplated. Introduction of an asparagine-X-serine or asparagine-X-threonine motif creates a potential site for enzymatic attachment of carbohydrate moieties and may therefore be used to manipulate the glycosylation of an antibody. In Raju et al (2001) Biochemistry 40, 8868-8876 the terminal sialyation of a TNFR-IgG immunoadhesin was increased through a process of regalactosylation and/or resialylation using beta-1,4-galactosyltransferace and/or alpha, 2,3 sialyltransferase. Increasing the terminal sialylation is believed to increase the half-life of the immunoglobulin. Antibodies, in common with most glycoproteins, are typically produced in nature as a mixture of glycoforms. This mixture is particularly apparent when antibodies are produced in eukaryotic, particularly mammalian cells. A variety of methods have been developed to manufacture defined glycoforms, see Zhang et al Science (2004), 303, 371, Sears et al, Science, (2001) 291, 2344, Wacker et al (2002) Science, 298 1790, Davis et al (2002) Chem. Rev. 102, 579, Hang et al (2001) Acc. Chem. Res 34, 727. Thus the invention may utilise a plurality of therapeutic antibodies (which maybe of the IgG isotype, e.g. IgG1) as described herein comprising a defined number (e.g. 7 or less, for example 5 or less such as two or a single) glycoform(s) of said antibodies.

Derivatives useful in the invention also include therapeutic antibodies coupled to a non-proteinaeous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments, see Koumenis I. L. et al (2000) Int. J. Pharmaceul. 198:83-95. A particular embodiment comprises an antigen-binding fragment of a therapeutic antibody without the effector functions of a) activation of complement by the classical pathway; and b) mediating antibody-dependent cellular cytotoxicity; (such as a Fab fragment or a scFv) coupled to PEG.

2. Production Methods

Antigen binding proteins, specifically antibodies, useful in the present invention may be produced in transgenic organisms such as goats (see Pollock et al (1999), J. Immunol. Methods 231:147-157), chickens (see Morrow K J J (2000) Genet. Eng. News 20:1-55), mice (see Pollock et al ibid) or plants (see Doran P M, (2000) Curr. Opinion Biotechnol. 11, 199-204, Ma J K-C (1998), Nat. Med. 4; 601-606, Baez J et al, BioPharm (2000) 13: 50-54, Stoger E et al; (2000) Plant Mol. Biol. 42:583-590). Antigen binding proteins, e.g. antibodies, may also be produced by chemical synthesis. However, antibodies useful in the invention are typically produced using recombinant cell culturing technology well known to those skilled in the art. A polynucleotide encoding the antibody is isolated and inserted into a replicable vector such as a plasmid for further propagation or expression in a host cell. One useful expression system is a glutamate synthetase system (such as sold by Lonza Biologics), particularly where the host cell is CHO or NSO (see below). Polynucleotide encoding the antibody is readily isolated and sequenced using conventional procedures (e.g. oligonucleotide probes). Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotide encoding the light and heavy chains may be inserted into separate vectors and introduced (e.g. by transformation, transfection, electroporation or transduction) into the same host cell concurrently or sequentially or, if desired both the heavy chain and light chain can be inserted into the same vector prior to such introduction.

It will be immediately apparent to those skilled in the art that due to the redundancy of the genetic code, alternative polynucleotides to those disclosed herein are also available that will encode the polypeptides useful in the invention.

2.1 Signal Sequences

Antigen binding proteins, e.g. antibodies, useful in the present invention maybe produced as a fusion protein with a heterologous signal sequence having a specific cleavage site at the N terminus of the mature protein. The signal sequence should be recognised and processed by the host cell. For prokaryotic host cells, the signal sequence may be an alkaline phosphatase, penicillinase, or heat stable enterotoxin II leaders. For yeast secretion the signal sequences may be a yeast invertase leader, a factor leader or acid phosphatase leaders see e.g. WO90/13646. In mammalian cell systems, viral secretory leaders such as herpes simplex gD signal and native immunoglobulin signal sequences (such as human Ig heavy chain) are available. Typically the signal sequence is ligated in reading frame to polynucleotide encoding the therapeutic antigen binding protein useful in the invention.

2.2 Origin of Replication

Origin of replications are well known in the art with pBR322 suitable for most gram-negative bacteria, 2μ plasmid for most yeast and various viral origins such as SV40, polyoma, adenovirus, VSV or BPV for most mammalian cells. Generally the SV40 origin of replication component is not needed for integrated mammalian expression vectors. However the SV40 on may be included since it contains the early promoter.

2.3 Selection Marker

Typical selection genes encode proteins that (a) confer resistance to antibiotics or other toxins e.g. ampicillin, neomycin, methotrexate or tetracycline or (b) complement auxotrophic deficiencies or supply nutrients not available in the complex media or (c) combinations of both. The selection scheme may involve arresting growth of the host cells that contain no vector or vectors. Cells, which have been successfully transformed with the genes encoding the therapeutic antibody useful in the present invention, survive due to e.g. drug resistance conferred by the co-delivered selection marker. One example is the DHFR-selection system wherein transformants are generated in DHFR negative host strains (eg see Page and Sydenham 1991 Biotechnology 9: 64-68). In this system the DHFR gene is co-delivered with antibody polynucleotide sequences and DHFR positive cells then selected by nucleoside withdrawal. If required, the DHFR inhibitor methotrexate is also employed to select for transformants with DHFR gene amplification. By operably linking DHFR gene to the antibody coding sequences of the therapeutic antibody or functional derivatives thereof, DHFR gene amplification results in concomitant amplification of the desired antibody sequences of interest. CHO cells are a particularly useful cell line for this DHFR/methotrexate selection and methods of amplifying and selecting host cells using the DHFR system are well established in the art see Kaufman R. J. et al J. Mol. Biol. (1982) 159, 601-621, for review, see Werner R G, Noe W, Kopp K, Schluter M, "Appropriate mammalian expression systems for biopharmaceuticals", Arzneimittel-Forschung. 48(8):870-80, 1998 August. A further example is the glutamate synthetase expression system (Bebbington et al Biotechnology 1992 Vol 10 p 169). A suitable selection gene for use in yeast is the trp1 gene; see Stinchcomb et al Nature 282, 38, 1979.

2.4 Promoters

Suitable promoters for expressing antibodies are operably linked to DNA/polynucleotide encoding the antigen binding protein, e.g. antibody. Promoters for prokaryotic hosts include phoA promoter, Beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceralderhyde 3 phosphate dehydrogenase, hexokinase, pyruvate decarboxylase, phosphofructokinase, glucose 6 phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include RNA polymerase II promoters including viral promoters such as polyoma, fowlpox and adenoviruses (e.g. adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40 and non-viral promoters such as EF-1alpha (Mizushima and Nagata Nucleic Acids Res 1990 18(17):5322. The choice of promoter may be based upon suitable compatibility with the host cell used for expression.

2.5 Enhancer Element

Where appropriate, e.g. for expression in higher eukaroytics, additional enhancer elements can be included instead of or as well as those found located in the promoters described above. Suitable mammalian enhancer sequences include enhancer elements from globin, elastase, albumin, fetoprotein, metallothionine and insulin. Alternatively, one may use an enhancer element from a eukaroytic cell virus such as SV40 enhancer, cytomegalovirus early promoter enhancer, polyoma enhancer, baculoviral enhancer or murine IgG2a locus (see WO04/009823). Whilst such enhancers are typically located on the vector at a site upstream to the promoter, they can also be located elsewhere e.g. within the untranslated region or downstream of the polydenalytion signal. The choice and positioning of enhancer may be based upon suitable compatibility with the host cell used for expression.

2.6 Polydenalytion/Termination

In eukaryotic systems, polyadenylation signals are operably linked to polynucleotide encoding the antibody. Such signals are typically placed 3' of the open reading frame. In mammalian systems, non-limiting example signals include those derived from growth hormones, elongation factor-1 alpha and viral (e.g. SV40) genes or retroviral long terminal repeats. In yeast systems non-limiting examples of polydenylation/termination signals include those derived from the phosphoglycerate kinase (PGK) and the alcohol dehydrogenase 1 (ADH) genes. In prokaryotic system polyadenylation signals are typically not required and it is instead usual to employ shorter and more defined terminator sequences. The choice of polyadenylation/termination sequences may be based upon suitable compatibility with the host cell used for expression.

2.7 Other Methods/Elements for Enhanced Yields

In addition to the above, other features that can be employed to enhance yields include chromatin remodelling elements, introns and host-cell specific codon modification. The codon useage of the antibody can be modified to accommodate codon bias of the host cell such to augment transcript and/or product yield (eg Hoekema A et al Mol Cell Biol 1987 7(8):2914-24). The choice of codons may be based upon suitable compatibility with the host cell used for expression.

2.8 Host Cells

Suitable host cells for cloning or expressing vectors encoding antibodies are prokaroytic, yeast or higher eukaryotic cells. Suitable prokaryotic cells include eubacteria e.g. enterobacteriaceae such as *Escherichia* e.g. *E. Coli* (for example ATCC 31,446; 31,537; 27,325), *Enterobacter, Erwinia, Klebsiella Proteus, Salmonella* e.g. *Salmonella typhimurium, Serratia* e.g. *Serratia marcescans* and *Shigella* as well as *Bacilli* such as *B. subtilis* and *B. licheniformis* (see DD 266 710), Pseudomonas such as *P. aeruginosa* and *Streptomyces*. Of the yeast host cells, *Saccharomyces cerevisiae, schizosaccharomyces pombe, Kluyveromyces* (e.g. ATCC 16,045; 12,424; 24178; 56,500), *yarrowia* (EP402, 226), *Pichia Pastoris* (EP183,070, see also Peng et al J. Biotechnol. 108 (2004) 185-192), *Candida, Trichoderma reesia* (EP244, 234), *Penicillin, Tolypocladium* and *Aspergillus* hosts such as *A. nidulans* and *A. niger* are also contemplated.

Although Prokaryotic and yeast host cells are specifically contemplated, typically however, host cells are vertebrate cells. Suitable vertebrate host cells include mammalian cells such as COS-1 (ATCC No. CRL 1650) COS-7 (ATCC CRL 1651), human embryonic kidney line 293, PerC6 (Crucell), baby hamster kidney cells (BHK) (ATCC CRL. 1632), BHK570 (ATCC NO: CRL 10314), 293 (ATCC NO. CRL 1573), Chinese hamster ovary cells CHO (e.g. CHO-K1, ATCC NO: CCL 61, DHFR minus CHO cell line such as DG44 (Urlaub et al, Somat Cell Mol Genet (1986) Vol 12 pp 555-566), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NSO (see U.S. Pat. No. 5,807,715), Sp2/0, Y0.

A stably transformed host cell may comprise a vector encoding a heavy chain and/or light chain of the therapeutic antibody as described herein. Typically such host cells comprise a first vector encoding the light chain and a second vector encoding said heavy chain.

Such host cells may also be further engineered or adapted to modify quality, function and/or yield of the antigen binding protein, e.g. antibody. Non-limiting examples include expression of specific modifying (e.g. glycosylation) enzymes and protein folding chaperones.

2.9 Cell Culturing Methods.

Host cells transformed with vectors encoding therapeutic antigen binding proteins, e.g. antibodies, may be cultured by any method known to those skilled in the art. Host cells may be cultured in spinner flasks, shake flasks, roller bottles, wave reactors (e.g. System 1000 from wavebiotech.com) or hollow fibre systems but it is preferred for large scale production that stirred tank reactors or bag reactors (e.g. Wave Biotech, Somerset, N.J. USA) are used particularly for suspension cultures. Typically the stirred tankers are adapted for aeration using e.g. spargers, baffles or low shear impellers. For bubble columns and airlift reactors direct aeration with air or oxygen bubbles maybe used. Where the host cells are cultured in a serum free culture media this can be supplemented with a cell protective agent such as pluronic F-68 to help prevent cell damage as a result of the aeration process. Depending on the host cell characteristics, either microcarriers maybe used as growth substrates for anchorage dependent cell lines or the cells maybe adapted to suspension culture (which is typical). The culturing of host cells, particularly vertebrate host cells may utilise a variety of operational modes such as batch, fed-batch, repeated batch processing (see Drapeau et al (1994) cytotechnology 15: 103-109), extended batch process or perfusion culture. Although recombinantly transformed mammalian host cells may be cultured in serum-containing media such media comprising fetal calf serum (FCS), it is preferred that such host cells are cultured in serum-free media such as disclosed in Keen et al (1995) Cytotechnology 17:153-163, or commercially available media such as ProCHO-CDM or UltraCHO™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg K et al (1995) in *Animal Cell technology: Developments towards the 21st century* (Beuvery E. C. et al eds), pp 619-623, Kluwer Academic publishers).

Antigen binding proteins, e.g. antibodies, secreted into the media may be recovered and purified from the media using a variety of techniques to provide a degree of purification suitable for the intended use. For example the method of treatment of the invention of human patients typically mandates at least 95% purity as determined by reducing SDS-PAGE, more typically 98% or 99% purity, when compared to the culture media comprising the therapeutic antibodies. In the first instance, cell debris from the culture media is typically removed using centrifugation followed by a clarification step of the supernatant using e.g. microfiltration, ultrafiltration and/or depth filtration. Alternatively, the antibody can be harvested by microfiltration, ultrafiltration or depth filtration without prior centrifugation. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. In one embodiment, the antibodies useful in the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g. nanofiltration using e.g. a DV-20 filter). Following these various steps, a purified (typically monoclonal) preparation comprising at least 10 mg/ml or greater e.g. 100 mg/ml or greater of the antibody is provided and is useful in the invention. Concentration to 100 mg/ml or greater can be generated by ultracentrifugation. Suitably such preparations are substantially free of aggregated forms of antibodies.

Bacterial systems are particularly suited for the expression of antibody fragments. Such fragments are localised intracellularly or within the periplasma. Insoluble periplasmic proteins can be extracted and refolded to form active proteins according to methods known to those skilled in the art, see Sanchez et al (1999) J. Biotechnol. 72, 13-20 and Cupit P M et al (1999) Lett Appl Microbiol, 29, 273-277.

3. Pharmaceutical Compositions

Purified preparations of antigen binding proteins, e.g. antibodies, useful in the invention (particularly monoclonal preparations) as described supra, may be incorporated into pharmaceutical compositions for use in the treatment of human diseases and disorders such as those outlined above. Typically such compositions further comprise a pharmaceutically acceptable (i.e. inert) carrier as known and called for by acceptable pharmaceutical practice, see e.g. Remingtons Pharmaceutical Sciences, 16th ed, (1980), Mack Publishing Co. Examples of such carriers include sterilised carrier such as saline, Ringers solution or dextrose solution, buffered with suitable buffers such as sodium acetate trihydrate to a pharmaceutically acceptable pH, such as a pH within a range of 5 to 8. Pharmaceutical compositions for injection (e.g. by intravenous, intraperitoneal, intradermal, subcutaneous, intramuscular, intraportal or by local delivery to the eye by topical or periocular application to the eye or intravitreal injection into the eye) or continuous infusion are suitably free of visible particulate matter and may comprise from 1 mg to 10 g of therapeutic antibody, typically 5 mg to 1 g, more specifically 5 mg to 25 mg or 50 mg of antibody. Methods for the preparation of such pharmaceutical compositions are well known to those skilled in the art. In one embodiment, pharmaceutical compositions comprise from 1 mg to 10 g of therapeutic antibodies useful in the invention in unit dosage form, optionally together with instructions for use. Pharmaceutical compositions useful in the invention may be lyophilised (freeze dried) for reconstitution prior to administration according to methods well known or apparent to those skilled in the art. Where embodiments of the invention comprise antibodies with an IgG1 isotype, a chelator of metal ions including copper, such as citrate (e.g. sodium citrate) or EDTA or histidine, may be added to the pharmaceutical composition to reduce the degree of metal-mediated degradation of antibodies of this isotype, see EP0612251. Pharmaceutical compositions may also comprise a solubiliser such as arginine base, a detergent/anti-aggregation agent such as polysorbate 80, and an inert gas such as nitrogen to replace vial headspace oxygen.

Effective doses and treatment regimes for administering the antibody according to the method of the invention are generally determined empirically and are dependent on factors such as the age, weight and health status of the patient and disease or disorder to be treated. Such factors are within the purview of the attending physican. Guidance in selecting appropriate doses may be found in e.g. Smith et al (1977) Antibodies in human diagnosis and therapy, Raven Press, New York but will in general be 1 mg to 10 g. In one embodiment, the dosing regime for treating a human patient is 1 mg to 1 g of therapeutic antibody administered subcutaneously once per week or every two weeks, or by intravenous infusion every 1 or 2 months. Such a dosage corresponds to 0.014-140 mg/kg, such as 0.014-14 mg/kg. Compositions useful in the present invention may also be used prophylactically.

Compositions may also be delivered more locally to the eye either by topical application, intravitreal injection or periocular administration, i.e. subsclerally via either retrobulbar, peribulbar, subtenon or subconjunctival injection. Systemic administration may be sufficient to achieve drusen reduction via passive, e.g. intravenous administration of the therapeutic antibody. Other routes of local administration may allow the therapeutic antibody to reach the posterior segment of the eye more readily at lower doses. Topical application has been described to allow penetrance of antibody fragments to the posterior of the eye in the rabbit model, (Williams K A et al., (2005)). Intravitreal injection of antibody fragments or full monoclonal antibodies has been described and is well-tolerated for AMD patients for the products ranibizumab and bevacizumab. Therapeutic antibody may also be administered by an intravitreal implant. Retrobulbar and peribulbar injections can be achieved with special 23 to 26 gauge needles and are less invasive than intravitreal injections. Subtenon injection places the composition in contact with the sclera for a longer period which could aid penetration to the posterior eye. Injection of proteins just beneath the conjuctiva has been described in rabbit models and this allows molecules to diffuse more directly across the sclera to reach the posterior segment of the eye. Sustained release drug delivery systems may also be used which allow for release of material over a longer time-frame into or around the eye so that dosing could be less frequent. Such systems include micelles, gels, hydrogels, nanoparticles, microcapsules or implants that can be filled or coated with therapeutic compositions. These may be delivered into the vitreous of the eye by injection or by any of the other previously described less invasive routes, i.e. through the periocular or sub-scleral routes. Examples of such sustained release systems and local delivery routes include thermosensitive slow release hydrogels for subscleral administration or intravitreal administration of a nanoparticle based formulation that targets to the posterior retina and RPE layer (Janoira K G, et al., (2007); Birch D G (2007)). Many other combinations of delivery system and local administration route are possible and could be considered for compositions of therapeutic antibody.

4. Clinical Uses.

It will be appreciated that diseases or disorders affecting the eye or optic nerve characterised by elevated β-amyloid levels or β-amyloid deposits, include age related macular degeneration and glaucoma type diseases and β-amyloid dependent cataract formation.

Although the present invention has been described principally in relation to the treatment of human diseases or disorders, the present invention may also have applications in the treatment of similar diseases or disorders in non-human mammals.

Examples

| Methods | |
|---|---|
| Biacore ™/Biacore 3000 | a device that allows measurement of real time kinetics of molecular interactions using SPR |
| SPR | (surface plasmon resonance)—physical phenomenon employed by Biacore ™ instruments for measurement of mass changes on sensor chip |
| CM5 | Biacore ™ sensor chip with general purpose surface coated with a carboxymethylated dextran matrix |
| ELISA | enzyme linked immunosorbent assay |
| SRU | SRU BIND ™ Biosensor technology allowing to monitor label-free biochemical interactions |
| Integra CL1000 | Mini-bioreactors sold by IBS Integra Biosciences |
| FMAT | fluorometric microvolume assay technology (Applied Biosystems) |
| ABi8200 | Applied Biosystems 8200 fluorescence macro confocal cellular detection system for FMAT |
| FPLC | Fast protein liquid chromatography |
| ProSepA HiTrap | Protein A columns for FPLC sold by GE Healthcare |

| Materials | |
|---|---|
| DMSO | dimethylsulphoxide |
| HEPES | N-(2-hydroxyethyl)piperazine-N'-(2-ethanesulfonic acid) |
| EDTA | ethylenediaminetetraacetic acid |
| Tris HCl- | tris-(hydroxymethyl)aminomethane hydrochloride |
| NaCl- | sodium chloride |
| Tween-20- | polyoxyethylenesorbitan monolaurate |
| BSA- | bovine serum albumin |
| PBS- | phosphate buffered saline |
| PFA- | paraformaldehyde |
| IMS- | industrial methylated spirit |
| DAB- | 3,3'diaminobenzidine |
| DMEM | dulbecco's modified eagle's medium |
| FCS | fetal calf serum |
| Opti-MEM | modified eagle's medium based medium by Invitrogen/Gibco |
| Lipofectamine | cationic lipid based cell transfection agent sold by Invitrogen/Gibco |
| Transfast | liposomal transfection agent sold by Promega |
| Versene | metal ion chelating agent (ethylenediaminetetraacetic acid) |
| Glutamax | stable form of glutamine added to culture medium (dipeptide L-Ananyl-L-Glutamine supplement) |
| Histoclear | tissue clearing agent |
| HBS-EP buffer | General purpose Biacore ™ buffer containing 0.01M HEPES pH7.4, 0.15M NaCl, 3 mM EDTA, 0.005% Surfactant P20 |

Generation of Mouse Monoclonal Antibody 2E7

Mouse monoclonal antibody 2E7 was generated from a conventional immunisation of mice. Mice were immunised with soluble or aggregated β-amyloid 1-40 and 1-42 formulated in Freund's adjuvant. Following final boost without adjuvant, splenocytes were fused with myeloma cells. Fused cells were grown in 96-well plates from which hybridoma supernatants were screened for potential leads. Selected antibody 2E7, which was obtained from the immunisation with soluble β-amyloid 1-40, was of murine IgG2a isotype and had beta-amyloid binding activity in the $I^{125}$ β-amyloid in vivo binding assay described below and an affinity of 36.1 pM for beta-amyloid 1-40 when measured by Biacore™, Method A(i) (Table 10A).

Epitope Mapping of 2E7

In order to finely map the binding of antibody 2E7 to the β-amyloid peptide, a peptide set (A) was utilised. Peptide set (A) consisted of a set of 31 12-mer overlapping peptides covering the complete sequence of the β-amyloid 1-42 peptide. Each sequential peptide was initiated at the sequential amino acid within the β-amyloid peptide, thus shifting the sequence covered between sequential peptides by a single amino acid. All peptides in set (A) contained a 3 amino acid C-terminal linker (glycine-serine-glycine) and a terminal biotinylated lysine residue. In addition, all peptides except peptide Aβ1 DAEFRHDSGYEVGSGK-biotin (SEQ ID No:15) were N-terminally acetylated. A second set of peptides (set (B)) consisted of sequential one amino acid C-terminal deletions from a peptide containing amino acids 1 to 10 of the β-amyloid sequence. All peptides in set (B) contained a 3 amino acid C-terminal linker (glycine-serine-glycine) and a terminal biotinylated lysine residue, but with additional glycine and serine residues to replace for deleted β-amyloid amino acids (Table 2). Thus all peptides in set (B) are of the same length.

TABLE 2

Sequences of biotinylated peptides (set(B)) that contained truncated N-terminal fragments of β-amyloid

| Sequence | ID |
|---|---|
| DAEFRHDSGYGSGGSK-biotin | (SEQ ID No: 7) |
| DAEFRHDSG--GSGSGSK-biotin | (SEQ ID No: 8) |
| DAEFRHDS--GSGGSGGK-biotin | (SEQ ID No: 9) |
| DAEFRHD--GSGGSGGSK-biotin | (SEQ ID No: 10) |
| DAEFRH--GSGGSGSGSK-biotin | (SEQ ID No: 11) |
| DAEFR--GSGGSGGSGSK-biotin | (SEQ ID No: 12) |
| DAEF--GSGGSGGSGGSK-biotin | (SEQ ID No: 13) |
| DAE--GSGGSGGSGGSK-biotin | (SEQ ID No: 14) |

Monitoring the Binding of 2E7 to β-amyloid Derived Peptides Using Optical Biosensors 96-well SRU Bind™ streptavidin-coated plates (SRU Biosystems) were washed with PBS containing 1% DMSO to remove glycerol and preservative. A volume of 50 ul/well was left to equilibrate to room temperature to provide a constant base line. Biotinylated peptides were diluted to approx. 0.3 ug/ml in PBS containing 1% DMSO and 50 ul of each added to wells and incubated for approximately 1 h. Replicate wells were prepared using different sectors of the plate and at least one no-peptide control well was used in each sector to reference subtract the data. After peptide capture the plate was washed with PBS containing 1% DMSO, leaving 50 ul of fresh buffer per well to provide a new base line on the reader. No decay of peptide from the surface was seen. The buffer was then replaced with 40 ul/well buffer containing test antibody at 20-64 nM for 2 hours. It was found that antibody 2E7 only bound to the peptide encompassing amino acids 1-12 of the β-amyloid peptide in peptide set (A) (peptide Aβ1, SEQ ID No:15) This result implies that the aspartic acid at residue 1 is critical for binding to this peptide.

In order to further characterise the binding site of antibody 2E7, peptide set (B) was utilised. Using SRU BIND™ biosensor methodology antibody 2E7 showed negligible binding to the peptides encompassing amino acids 1-3 and 1-4 of the β-amyloid peptide (SEQ ID No:14 and 13). Binding to a peptide encompassing amino acids 1-7 of the β-amyloid peptide (SEQ ID No:10) was comparable to the peptide encompassing amino acids 1-12 of the β-amyloid peptide (from peptide set (A)). Binding to peptides encompassing amino acids 1-5 or 1-6 of the β-amyloid peptide (SEQ ID No:12 or 11) was observed, but was weaker (as measured by stability after an additional washing step) than the binding to the peptide encompassing amino acids 1-7 of the β-amyloid peptide (SEQ ID No:10).

Thus it has been shown that only residues 1-7 of the β-amyloid peptide are required for full binding as measured using this methodology.

Surface Plasmon Resonance Assay

In addition to the experiments described above, the Biacore™ 3000 optical biosensor was used to monitor the binding of 2E7 antibody to selected β-amyloid sequence derived peptides. Binding was measured by injecting test antibodies at up to 64 nM for 5 minute over peptides captured on separate streptavidin chip surfaces (130-230 RU (resonance units)). A running buffer (HBS-EP) containing 0.01 M HEPES pH7.4, 0.15 M NaCl, 3 mM EDTA and 0.005% Surfactant P20™ at 25° C. was used at a flow rate of 20 ul/min. All runs were double referenced against a blank streptavidin surface and blank injections. Analysis was carried out using the Biacore™ analysis software BIAevaluation™ version 4.1. Results from selected peptides in set (A) further confirmed the SRU BIND™ derived data indicating that 2E7 bound only to the peptide encompassing amino acids 1-12 (SEQ ID No:15) of the β-amyloid peptide with an apparent equilibrium constant KD of approximately 50 pM. Under the same conditions, 2E7 did not bind to the peptide encompassing amino acids 2-13 of the β-amyloid peptide.

Peptide Aβ2-13
AEFRHDSGYEVHGSGK-biotin        (SEQ ID No: 44)

The experimental method and conditions used allowed the detection of high but also lower affinity molecules—in the same experimental setup, by contrast to 2E7, another antibody recognising an N-terminal epitope of the β-amyloid peptide was shown to bind the 2-13 peptide (SEQ ID No:44) with an apparent KD of 7 nM. 2E7 did not bind to a selection of peptides in set (A) from mid regions of the β-amyloid peptide. In a separate experiment the β-amyloid 1-40 peptide was captured via its N-terminal aspartic acid residue that had been biotinylated. This peptide was captured onto a Biacore™ streptavidin coated chip as previously described. Antibody 2E7 injected at 66 nM for 1 minute could not bind this peptide. Therefore, it is concluded that the previously described N-terminal binding site was masked by the linker and capture method, thus further confirming the extreme N-terminus as containing the core binding site.

Binding to Cell Expressed Amyloid Precursor Protein (APP)

β-Amyloid is composed of peptides formed by proteolytic cleavage of a type I transmembrane precursor protein named amyloid precursor protein (APP). As APP has a large extracellular domain, binding to this protein could potentially initiate an antibody-dependent cellular cytotoxicity reaction (ADCC).

To characterise binding of antibody to cell-surface full length APP an FMAT™ ABI8200 based assay was utilised.

Transfection of HEK293T Cells with Wild Type APP DNA

HEK293T cells are maintained in DMEM F12 medium containing 10% (v/v) FCS and 1× Glutamax. Cells are seeded in 75 $cm^2$ tissue culture flasks and grown to 60-80% confluency (18-24 h) prior to transfection. For transfection, 9 ug of DNA, (either wild type APP DNA (in PCDNA3.1 (Invitrogen) vector), or vector only controls), is mixed with 0.3 ml of Opti-MEM™ media. 30 ul Lipofectamine™ transfection agent is mixed with 0.3 ml Opti-MEM™ media and the two mixtures pooled. The pooled mixtures are incubated at room temperature for 30 min prior to the addition of a further 4.8 ml of Opti-MEM™ media. The final mixture is added to the cells (post washing with Opti-MEM™ media) for 5 h and 6 ml of 10% (v/v) newborn calf serum in DMEM is then added. 48 hrs post transfection, supernatant is removed and the monolayer washed in versene, and then 3 ml of Versene™ chelating agent is added to each flask, incubated for 5 mins at 37 C, and the detached cells pelleted at 200 g for 5 mins. The resultant cell pellet is gently resuspended in 1 ml of assay buffer (2% heat treated serum, 0.5% BSA, 0.1% $NaN_3$ in PBS pH7.4, filtered through a 0.2 um filter) to create a single cell suspension.

FMAT™ ABI8200 Based Assay

Test antibodies (2E7, LN27 (Zymed) mouse IgG to extracellular domain of APP as a positive control, and an antibody G210 which recognises the x-40 form of the β-amyloid peptide as a negative control) were diluted to 10 μg/ml in sterile filtered assay buffer (2% heat treat serum, 0.5% BSA, 0.1% $NaN_3$ in PBS pH7.2) in a polypropylene plate, and then a further six serial 1:1 dilutions were performed down the plate. Assay buffer only was used as a blank. 50 ul of a suspension of HEK293T cells transfected with wild type APP DNA (Experiment 1: 10,000 cells; Experiment 2: 20,000 cells) was added to each well of a 96 well plate, to which 5 ul of each of the antibody solutions were added to duplicate wells. 50 ul/well of F-MAT™ blue anti mouse IgG stock, (antibody is labelled using F-MAT™ blue monofunctional reactive dye kit from ABI, 4328408), diluted 1:500 (Experiment 1) and 1:1000 (Experiment 2) in assay buffer, was then added to each well and the plate briefly shaken and left to settle for 1 hr. The plate was then read using the ABI 8200 fluorescence macro confocal cellular detection system (Applied Biosystems).

Derived counts data were then interpreted using Excel™ spreadsheet software. Briefly, mock transfected counts were subtracted from the full length APP transfected cell counts to obtain a specific signal for each antibody. Two antibody concentrations that were on the linear part of the curve were chosen (1.25 and 0.63 ug/ml) and the background corrected derived counts at these concentrations expressed as the percentage of the LN27 antibody binding, and averaged over the two antibody concentrations. The resultant data is described in Table 3 (% of LN27 binding±SE)

Thus, within this assay system, the binding of 2E7 to cell surface APP is indistinguishable from that of the negative control antibody G210.

TABLE 3

| antibody | Experiment 1 | Experiment 2 |
|---|---|---|
| LN27 | 100.0 ± 7.1 | 100.0 ± 4.7 |
| G210 | 5.5 ± 1.3 | 2.0 ± 1.6 |
| 2E7 | 9.9 ± 3.7 | 2.2 ± 1.4 |

Binding to Amyloid Precursor Protein Derived Peptide

The previously described epitope mapping studies have shown that antibody 2E7 binds to the extreme N-terminus of the β-amyloid peptide, with the aspartic acid residue at position 1 being essential for binding. This suggests that the antibody recognises a 'neo' epitope formed by cleavage of APP at the β-secretase site. This observation would suggest that antibody 2E7 should not recognise adjacent APP peptide sequence. To test this hypothesis an APP peptide (Peptide APP1, SEQ ID No:16) was synthesised which included residues 1-7 of the β-amyloid peptide and the five adjacent APP derived amino acids. Thus peptide APP1 contained contiguous amino acids from position 5 N-terminal to the BACE-1 cleavage site to position 7 C-terminal to the BACE-1 cleavage site and was N-terminally acetylated. The ability of antibody 2E7 to bind to the APP derived peptide APP1 and the β-amyloid 1-12 peptide (peptide Aβ1) was compared using Biacore™ methodology (as previously described for epitope mapping). Antibody 2E7 showed high affinity binding to the β-amyloid peptide Aβ-1, which contains the basic epitope 1-7. However, no binding was observed to the APP1 peptide which also contains the basic β-amyloid derived sequence 1-7.

```
Peptide Aβ1
DAEFRHDSGYEVGSGK-biotin        SEQ ID No: 15

APP1
AcNH-SEVKMDAEFRHDGSGK-biotin   SEQ ID No: 16
```

A combination of FMAT™ based cellular binding and Biacore™ based peptide mapping has been utilised to show that, in these formats, 2E7 has no binding affinity for the full length APP protein. Given that the aspartic acid residue at position 1 of the β-amyloid peptide is required for binding, it is concluded that 2E7 only recognises the 'neo' N-terminus of β-amyloid and hence should not bind cell surface expressed APP.

In Vivo Binding Activity Using $I^{125}$ β-Amyloid

A number of published studies have shown that β-amyloid antibodies can form complexes with β-amyloid peptide in the bloodstream. It has been argued that this sequestration of peripheral β-amyloid leads to increased levels of CNS derived amyloid in the bloodstream (DeMattos R B, PNAS (2001), 98(15); 8850-8855). An acute in vivo model was therefore developed to screen antibodies for their ability to complex synthetic β-amyloid peptide in the bloodstream.

Anaesthesia (4% isoflurane) was induced in male C57/BL6J mice and maintained (1.5% isoflurane) in 100% oxygen. Animals were then placed in a stereotaxic frame. Following midline incision along the sagittal suture a bore hole was drilled through the skull and a guide cannula was inserted into the lateral cerebral ventricle (coordinates anterioposterior (AP) −0.5 mm, lateral (L) +0.7 mm, ventral (V) −2.5 mm). A further two bore holes were drilled through the skull into which cortical screws were placed. The cannula was anchored in place by cyanoacrylate gel and the incision was sutured around the cyanoacrylate gel headcap. Post-operatively the mice received 0.3 ml saline subcutaneously and were placed in a warm environment to recover from anaesthesia. On recovery of the righting reflex, mice were housed singly and received 5 days standard post-op care. No procedures were permitted for a further 5 days or until pre-operative body weight was regained. Following recovery, cannula placement was verified by the angiotensin II drinking response. Each mouse received an intracerebroventricular (ICV) administration (5 μl) of 100 ng angiotensin II (AII) (made up in 0.9% saline). Following administration of AII, water intake was observed for 15 minutes. Mice with a positive dipsogenic response to AII (sustained drinking) were included in the studies, which commenced no sooner than five days post AII injection.

On the day of study the mice were placed for 5-10 minutes in a warm environment to induce vasodilation, necessary for ease of injection into the tail vein. Test antibody (600 µg) or PBS vehicle (dose volume no greater than 10 ml per kg body weight) was injected via the tail vein and mice were returned to their individual cages post-injection. At exactly one hour post tail vein injection, mice were slowly ICV injected (2 µl per minute) with 2 ng (1 µCi) of $I^{125}$ beta-amyloid 1-40 (Amersham Biosciences, UK) in a dose volume of 5 µl. At exactly four hours post ICV dose, 50 µl of trunk blood was collected and the radioactivity level measured on a scintillation counter.

Mice that had been injected into the tail-vein with 2E7 (n=6 per treatment group) showed a statistically significant increase in the radioactive signal (counts per minute—CPM) in 50 µl of trunk blood compared with the CPM signal detected in vehicle injected mice—(CPM—vehicle: 1339.7±496.2 vs. 2E7 4387.9±980.3; ANOVA:F(2,13)=4.97, p<0.05. Post-hoc LSD: p=0.01 2E7 vs. vehicle [post-hoc Duncans: p=0.02 2E7 vs, vehicle]).

In two further studies with 2E7 conducted with the identical protocol, similar increases in radioactive counts were detected in blood when compared with vehicle injected controls (CPM blood: Vehicle 352+/−113 versus 2E7 2397+/−353, and Vehicle 1281+/−312 versus 2E7 5291+/−885; ANOVA with post-hoc LSD test p<0.001 vs. vehicle).

Cloning of Hybridoma Variable Regions

Variable Region Sequences

Total RNA was extracted from 2E7 hybridoma cells and heavy and light variable domain cDNA sequences were then generated by reverse transcription and polymerase chain reaction (RT-PCR). The forward primer for RT-PCR was a mixture of degenerate primers specific for murine immunoglobulin gene leader-sequences and the reverse primer was specific for the antibody constant regions, in this case murine isotype IgG2a for the heavy chain and murine kappa for the light chain. Primers were designed according to the strategy described by Jones and Bendig (Bio/Technology 9:88, 1991). RT-PCR was carried out in duplicate for both V-region sequences to enable subsequent verification of the correct V-region sequences. The V-region products generated by RT-PCR were cloned (Invitrogen TA Cloning Kit) and sequence data obtained.

2E7 $V_H$ Amino Acid Sequence
(SEQ ID No: 17)
EVKLVESGGGLVQPGGSLKLSCAVSGFTFS<u>DNGMA</u>WVRQAPRKGPEWIA<u>F</u>

<u>ISNLAYSIDYADTVTG</u>RFTISRDNAKNTLYLEMSSLRSEDTAMYYCVS<u>GT</u>

<u>WFAY</u>WGQGTLVTVSA

2E7 $V_H$ DNA Sequence
(SEQ ID No: 18)
GAGGTGAAGCTGGTGGAGTCTGGGGGAGGCTTAGTGCAGCCTGGAGGGTC

CCTGAAACTCTCCTGTGCAGTCTCTGGATTCACTTTCAGTGACAACGGAA

TGGCGTGGGTTCGACAGGCTCCAAGGAAGGGGCCTGAGTGGATAGCGTTC

ATTAGTAATTTGGCATATAGTATCGACTACGCAGACACTGTGACGGGCCG

ATTCACCATCTCTAGAGATAATGCCAAGAATACCCTGTACCTGGAAATGA

GCAGTCTGAGGTCTGAGGACACGGCCATGTACTATTGTGTAAGCGGGACC

TGGTTTGCTTACTGGGGCCAAGGGACTCTGGTCACTGTCTCTGCA

2E7 $V_L$ Amino Acid Sequence
(SEQ ID No: 19)
DVVLTQTPLSLPVSLGDQASISC<u>RVSQSLLHSNGYTYLH</u>WYLQKPGQSPK LLIY<u>KVSNRFS</u>GVPDRFSGSGSGTDFTLKISRVEAEDLGVYFC<u>SQTRHVP</u>

<u>YT</u>FGGGTKLEIK

2E7 $V_L$ DNA Sequence
((SEQ ID No: 20)
GATGTTGTGCTGACCCAAACTCCACTCTCCCTGCCTGTCAGTCTTGGAGA

TCAAGCCTCCATCTCTTGCAGAGTTAGTCAGAGCCTTTTACACAGTAATG

GATACACCTATTTACATTGGTACCTGCAGAAGCCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTTCTGCTCTCAAACTAGACATGTTCCG

TACACGTTCGGAGGGGGGACCAAGCTGGAAATAAAA

Complementarity Determining Regions (CDRs) are underlined in the amino acid sequences.

Cloning and Expression of 2E7 Chimera

A chimeric 2E7 antibody (2E7c) consisting of the parent murine V regions grafted on to human IgG1 (Fc mutated (L235A, G237A)) for the heavy chain or human C kappa regions for the light chain was generated in order to express recombinant antibody material that could be used to confirm the correct cloning of functional murine V regions. DNA encoding 2E7 murine heavy and light chain V regions and endogenous murine signal sequences was cloned in frame into the mammalian expression vectors RLD-bshe (for the heavy chain) and RLN-bshe (for the light chain) already containing human constant regions (IgG1 Fc mutated (L235A, G237A) or human C kappa, respectively).

Elements of RLD-bshe expression vector for heavy chain expression:

| Base Pairs | Description of DNA segment |
| --- | --- |
| 0-1014 | Promoter (SV40/RSV) |
| 1015-2442 | Antibody heavy chain |
| 2443-2765 | Poly A |
| 2766-3142 | BG Promoter |
| 3239-3802 | DHFR |
| 3803-4162 | Poly A |
| 4163-6322 | Total backbone |
| 5077-5937 (complementary strand) | Beta lactamase |

(position of elements and overall size of vector given above are for illustration purposes only and will depend upon the size of the antibody chain insert)

Elements of RLN-bshe expression vector for light chain expression:

| Base Pairs | Description of DNA segment |
| --- | --- |
| 0-1014 | Promoter (SV40/RSV) |
| 1015-1731 | Antibody light chain |
| 1732-2051 | Poly A |
| 2388-2764 | BG Promoter |
| 2774-3568 | Neomycin |
| 3569-3876 | Poly A |

-continued

| Base Pairs | Description of DNA segment |
|---|---|
| 3877-6063 | Total backbone |
| 5077-5937 (complementary strand) | Beta lactamase |

(position of elements and overall size of vector given above are for illustration purposes only and will depend upon the size of the antibody chain insert)

Clones with correctly cloned $V_H$ and $V_L$ sequences were identified and plasmids prepared for expression in suspension culture CHO cells. Expressed 2E7c antibody was purified from cell culture supernatant by protein A chromatography on a FPLC system, and then tested for binding to AR by ELISA and SPR using Biacore™ technology. The results indicated that the correct 2E7 mouse V regions were cloned and expressed, resulting in a functional antibody with similar characteristics to the parent murine antibody 2E7.

Light Chain Humanisation

A human acceptor sequence with the Genpept ID CAA51135 (SEQ ID No:24) and Genbank Accesion No X72467, which had 77% identity on the amino acid level (including CDRs) was selected as the acceptor framework. Construct L1 is a graft of the murine CDRs from the 2E7 VL domain into this acceptor framework.

Heavy Chain Humanisation

Human sequence Genbank accession No M99675 (SEQ ID No:21) an allele of the VH3-48 gene with 74% identity on the amino acid level (including CDRs 1 and 2) to the 2E7 mouse variable heavy region was selected as the human heavy chain acceptor framework together with the human JH4 minigene. Three humanised variable heavy chain variants were designed based on the M99675 sequence and JH4. H1 is a graft of the murine CDRs using the Kabat definition with two additional framework back mutations at positions 93 and 94. H2 and H3 were both derived from H1, but incorporated one additional framework mutation which were different in each construct; (positions 24 and 48 respectively; see Table 4).

TABLE 4

| Construct | Template frameworks | Residue (Kabat#) | Human | Mouse |
|---|---|---|---|---|
| H1 | M99675 and JH4 | 93, 94 | A and R respectively | V and S respectively |
| H2 | H1 | 24 | A | V |
| H3 | H1 | 48 | V | I |

Construction of Humanised Heavy and Light Chain DNA

Humanised V regions were synthesised de novo by build up of overlapping oligos and PCR amplification. Restriction sites for cloning into mammalian expression vectors RLD-bshe and RLN-bshe and human immunoglobulin signal sequences derived from the chosen human acceptor frameworks were included. The DNAs encoding the humanised V regions (H1 (SEQ ID NO:27), H2 (SEQ ID NO:29), H3 (SEQ ID NO:31), L1 (SEQ ID NO:33)) together with signal sequences and restriction sites were then cloned in frame into mammalian expression vectors: H1, H2 and H3 into RLD-bshe to generate DNA encoding three full length human IgG1 Fc mutated heavy chains each containing mutations L235A and G237A, full length H1 (SEQ ID NO:35), full length H2 (SEQ ID NO:37) and full length H3 (SEQ ID NO:39); L1 was cloned in frame into RLN-bshe containing the DNA encoding human kappa constant region to generate DNA encoding a full length human kappa light chain (SEQ ID NO:41).

Representative Examples of Expression of Humanised Heavy and Light Chain Antibody Combinations CHOK1 cells were transiently transfected at small scale with all combinations of humanised light and heavy chain DNA constructs: L1+H1, L1+H2, L1+H3 (SEQ ID Nos: 35+41, 37+41, 39+41) in 6-well plates. CHOK1 cells passaged in DMEM F12, with 5% ultra low IgG foetal bovine serum and 2 mM glutamine were grown to confluency in 6-well plates. The confluent cells were transfected with a total of 7.5 µg DNA: 30 µg Transfast lipid (Promega) in Optimem Glutamax medium (Invitrogen). Transfected cells were incubated at 37° C. with 5% $CO_2$. At 72 hours supernatants were harvested and assayed for antibody concentration and then tested for binding to human Aβ by ELISA. Humanized L1 combined with the three humanized heavy chains all expressed complete antibody that bound to human Aβ.

Humanized antibodies were also expressed in large scale transient CHOK1 cell transfections using liposomal delivery of DNA (eg TransFast (Promega)) and expression in culture bottles. For optimization of expression levels in transient transfections a heavy to light chain expression vector DNA ratio of 1:6 was used. Material from transient transfection was purified using ProSepA columns or FPLC with ProSepA HiTrap columns.

Assessment of 2E7 Humanised Variants H1L1, H2L1 and H3 L1 in β-Amyloid Binding ELISA 2E7 H1L1, H2L1 and H3L1 humanised variants were assessed for binding to human Aβ peptide (1-40) biotinylated at the C terminus. The chimeric 2E7 was used as a reference. Tables 5-7 show results with various batches of purified material from large scale transient transfections.

TABLE 5

| ELISA | MAb | $EC_{50}$ (µg/ml) | Standard Error |
|---|---|---|---|
| Aβ binding | 2E7c Chimera | 0.033 | 0.00144 |
| | H1L1 | 0.035 | 0.00142 |
| | H2L1 | 0.048 | 0.00202 |
| | H3L1 | 0.044 | 0.00105 |

TABLE 6

| ELISA | MAb | $EC_{50}$ (µg/ml) | Standard Error |
|---|---|---|---|
| Aβ binding | 2E7c Chimera | 0.043 | 0.00183 |
| | H1L1 | 0.051 | 0.00164 |
| | H2L1 | 0.044 | 0.00191 |
| | H3L1 | 0.055 | 0.00094 |

TABLE 7

| ELISA | MAb | $EC_{50}$ (µg/ml) | Standard Error |
|---|---|---|---|
| Aβ binding | 2E7c Chimera | 0.044 | 0.00169 |
| | H1L1 | 0.047 | 0.00265 |
| | H2L1 | 0.041 | 0.00174 |
| | H3L1 | 0.040 | 0.00116 |

These results indicated very similar Aβ binding profiles for each of the 2E7-derived humanised variants. Comparison of the EC50 values to the 2E7c showed little loss of Aβ binding activity had been incurred through the humanization process.

Assessment of 2E7 Humanised Variant H2L1 Fab Fragment in β-Amyloid Binding ELISA A Fab fragment of H2L1 was generated by expressing truncated versions of the H2 heavy chain together with the L1 light chain in CHOK1 cells. The truncated versions of the H2 heavy chain were as follows: a) a version truncated at residue 224 of the hinge region, b) a version truncated at the second cysteine in the hinge region at residue 226 and c) a version truncated at position 224 with a C-terminal 6× histidine tag including histidine at position 224. An ELISA was carried out as above with culture supernatant containing expressed H2L1 Fab fragments of full H2L1 IgG. Results from two ELISA experiments in table 7A show that all Fab fragments bound to Aβ peptide (1-40) with very similar EC50 values.

TABLE 7A

| ELISA | Construct | $EC_{50}$ (µg/ml) | Standard Error |
|---|---|---|---|
| Aβ binding | H2L1 whole IgG | 0.113 | 0.00559 |
| | (a) H2L1 Fab | 0.239 | 0.02359 |
| | (b) H2L1 Fab cys | 0.226 | 0.01159 |
| | (c) H2L2 Fab His | 0.227 | 0.02440 |

Comparison of 2E7 Humanised Variants by Competition ELISA

2E7c chimeric and humanised antibodies H1 L1, H2L1 and H3L1 were assessed for their ability to inhibit the binding between the human Aβ peptide and the parental mouse 2E7 MAb in a competition ELISA.

Two types of competition ELISA were established in order to compare the Aβ binding activity of the three humanised variants compared to the 2E7 chimeric antibody. 1) Immobilised β-amyloid; biotinylated human Aβ peptide (1-40) was immobilized through Streptavidin on ELISA plates Mouse 2E7 antibody was added at a constant concentration along with a dilution series of 2E7-derived humanised variant antibodies. Bound mouse 2E7 MAb was then detected with anti-mouse IgG conjugate. Table 8 shows results of two assays.

TABLE 8

| Competitor MAb | Experiment 1 $IC_{50}$ (µg/ml) | Standard Error | Experiment 2 $IC_{50}$ (µg/ml) | Standard Error |
|---|---|---|---|---|
| 2E7c Chimera | 1.31 | 0.20 | 1.29 | 0.13 |
| H1L1 | 1.62 | 0.40 | 1.76 | 0.21 |
| H2L1 | 1.28 | 0.26 | 1.66 | 0.28 |
| H3L1 | 1.53 | 0.16 | 1.39 | 0.23 |

2) β-amyloid in solution; a constant concentration of β-amyloid was pre-incubated with a dilution series of humanised 2E7 antibody variants—the mixture including complexed and free amyloid was added for a short time to wells containing immobilised mouse 2E7 MAb. The amount of free β-amyloid that was still available for binding the immobilised parental 2E7 MAb was then detected. Table 9 shows results of two assays.

TABLE 9

| Competitor MAb | Experiment 1 $IC_{50}$ (µg/ml) | Standard Error | Experiment 2 $IC_{50}$ (µg/ml) | Standard Error |
|---|---|---|---|---|
| 2E7c Chimera | 0.052 | 0.006 | — | — |
| H1L1 | 0.114 | 0.014 | 0.140 | 0.024 |
| H2L1 | 0.075 | 0.009 | 0.119 | 0.014 |
| H3L1 | 0.069 | 0.004 | 0.115 | 0.013 |

All humanised antibody variants inhibited the binding of mouse 2E7 MAb to β-amyloid with a very similar profile. $IC_{50}$ values generated for H2L1 and H3L1 variants were consistently close to that of the 2E7c chimera (where used), which had the highest inhibitory activity in both assays. However, variant H1L1 showed a somewhat reduced inhibitory activity in both assays, indicating a possible slightly lower affinity for β-amyloid.

SPR Biacore™ Analysis of 2E7, 2E7c, H1L1, H2L1, H3L1

The kinetics parameters of recombinant mouse 2E7 MAb, chimeric 2E7c and humanized variants H1L1, H2L1 and H3L1 binding to human beta-amyloid peptide (1-40) and (1-42) were assessed using Biacore™ analysis on a Biacore™ 3000. Two different assay formats were used.

Method A (i) Briefly, <20 resonance units of beta-amyloid 1-40 peptide (biotinylated at the C-terminus) were captured on a streptavidin biosensor chip (as used for Table 10A). The antibodies were diluted down in HBS-EP buffer and passed over the streptavidin/beta-amyloid surface at concentrations ranging from 0.001 nM-8 nM (for Table 10A). Two separate runs were carried out; each run was carried out on a new streptavidin/beta-amyloid surface. Runs 1 and 2 were essentially the same though there were some differences in the parameters used; Run 1 was carried out using a chip surface on which 16 RU's of beta-amyloid were captured, and antibody concentrations of 0.001 nM-8 nM were used, an association time of 4 minutes and a dissociation time of 20 minutes were used at a flow rate of 50 µl per minute. For Run 2, less than 10 RU's of beta-amyloid were captured and antibody concentrations of 0.003125 nM-8 nM were used. The flow rate and association times were the same as Run 1, however the dissociation time was reduced to 15 minutes.

(ii) Beta amyloid (1-40) and (1-42) were amine-coupled on different surfaces of a CM5 biosensor chip to a level of <20 resonance units (as used for Table 10B). The antibodies were diluted down in HBS-EP buffer and passed over the biosensor/beta-amyloid surface at concentrations ranging from 1 nM-64 nM (as used for Table 10B).

Method B

In the second instance the assay was reversed, in that antibodies were first captured to a level of 1000-2500 resonance units on an anti-mouse IgG polyclonal antibody surface (for recombinant mouse 2E7 MAb) or a protein A surface (for humanized H2L1) of a CM5 biosensor chip. Freshly prepared beta-amyloid (1-40) or (1-42) was diluted down in HBS-EP buffer and passed over the captured-antibody surface at concentrations ranging from 4-500 nM (Table 10C and 10D).

In both methods, regeneration was via a pulse of 100 mM $H_3PO_4$, and for Table 10A data also followed by a pulse of 50 mM NaOH. The surface was shown to be stable and unaffected by regeneration. All runs were double referenced against buffer blank injections. Analysis was carried out using the Biacore™ analysis software BIAevaluation version 4.1.

Results

Method A(i) was used to rank order the antibodies by beta-amyloid binding kinetic data. The data obtained is shown in Table 10A. This shows that the parental 2E7 Mab has a KD of 36.1 pM for streptavidin-captured beta-amyloid. The chimeric mouse-human antibody showed a slightly reduced KD of 45.8 pM and the humanised constructs range from 54 (H2L1) to 93.6 pM (H1L1). In conclusion this demonstrates that the humanisation procedure had been very successful and very little affinity had been lost. The additional backmutations introduced for H2 and H3 had a small but beneficial effect, although the differences between H2 and H3 constructs are within the standard deviations for these experiments.

TABLE 10A

| Antibody | | ka | kd | KD(pm) |
|---|---|---|---|---|
| 2E7 | Run 1 | 1.61e6 | 6.17e−5 | 38.3 |
| | Run 2 | 1.69e6 | 5.72e−5 | 33.8 |
| | Average(SD) | 1.65e6 | 5.97e−5 | 36.1(3.2) |
| c2E7 | Run 1 | 1.34e6 | 6.44e−5 | 48.1 |
| | Run 2 | 1.3e6 | 5.65e−5 | 43.5 |
| | Average(SD) | 1.32e6 | 6.10e−5 | 45.8(3.3) |
| H1L1 | Run 1 | 5.60e5 | 5.32e−5 | 95.0 |
| | Run 2 | 6.37e5 | 5.87e−5 | 92.2 |
| | Average(SD) | 5.99e5 | 5.60e−5 | 93.6(2.0) |
| H2L1 | Run 1 | 9.91e5 | 5.76e−5 | 58.1 |
| | Run 2 | 1.1e6 | 5.49e−5 | 49.8 |
| | Average(SD) | 1.05e6 | 5.63e−5 | 54.0(5.9) |
| H3L1 | Run 1 | 8.24e5 | 6.26e−5 | 76.0 |
| | Run 2 | 8.3e5 | 4.75e−5 | 57.2 |
| | Average(SD) | 8.27e5 | 5.47e−5 | 66.6(13.3) |

Method A(ii) was used to confirm that the additional two amino-acid residues on the C-terminus of beta-amyloid (1-42) compared to beta-amyloid (1-40) did not significantly alter the binding properties of 2E7 and H2L1. The data obtained is shown in Table 10B and did confirm this.

TABLE 10B

| Antibody | Beta-amyloid | ka ($Ms^{-1}$) | kd ($s^{-1}$) | KD (pM) |
|---|---|---|---|---|
| 2E7 | 1-40 | 4.05e5 | 1.28e−4 | 317 |
| | 1-42 | 3.82e5 | 1.51e−4 | 394 |
| H2L1 | 1-40 | 3.33e5 | 1.22e−4 | 366 |
| | 1-42 | 3.40e5 | 1.55e−4 | 456 |

Method B was used to negate avidity effects potentially seen in the first assay format. Avidity effects, caused by both Fab domains of a single antibody molecule binding at the same time to two adjacent beta-amyloid molecules on the biosensor surface (or in multimeric forms of beta-amyloid), would increase the apparent affinity of binding. Affinity measurements obtained using Method B are shown in Table 10C.

TABLE 10C

| Antibody | ka ($Ms^{-1}$) | kd ($s^{-1}$) | KD (nM) With Standard Deviation n = 3 |
|---|---|---|---|
| 2E7 | 2.83e5 ± 0.54e5 | 4.28e−4 ± 0.65e−4 | 1.58 ± 0.55 |
| H2L1 | 1.06e5 ± 0.27e5 | 7.50e−4 ± 0.50 | 7.32 ± 1.64 |

Evidence that this assay provided true 1:1 binding affinities was obtained when Fab fragments of H2L1, obtained by papain digestion, bound streptavidin-captured beta-amyloid (1-40) by a similar method to Method A(i) with an estimated KD of 2.4 nM.

Method B was also used to confirm that the additional two amino-acid residues on the C-terminus of beta-amyloid (1-42) compared to beta-amyloid (1-40) did not significantly alter the binding properties of an identical sequence clone to mouse 2E7 MAb, named 2F11. The data obtained is shown in Table 10D.

TABLE 10D

| Antibody | Beta-amyloid | ka ($Ms^{-1}$) | kd ($s^{-1}$) | KD (nM) |
|---|---|---|---|---|
| 2F11 | 1-42 | 2.39e5 | 2.74e−4 | 1.14 |
| 2F11 | 1-40 | 2.99e5 | 3.92e−4 | 1.31 |

In a study similar to the epitope mapping study on 2E7 using the Surface Plasmon Resonance assay described above, H2L1 behaved similarly to 2E7 in binding to the peptide encompassing amino acids 1-12 (Aβ1, SEQ ID No:15) of the β-amyloid peptide and not to the peptide encompassing amino acids 2-13 of the β-amyloid peptide (Aβ2-13, SEQ ID No:44).

Activity of H2L1 in the $I^{125}$ β-Amyloid In Vivo Binding Assay

In order to functionally compare the humanised H2L1 with the parent mouse monoclonal 2E7, both were tested on the same day in the $I^{125}$ β-amyloid in vivo binding assay described above.

Both H2L1 and 2E7 significantly increased counts per minute (CPM) in blood compared with vehicle control. CPM of radioactivity in blood was as follows (Vehicle: 1940±166; 2E7: 10065±1386; H2L1: 10913±1535). Statistics used were ANOVA with post-hoc LSD test. n=7 vehicle, n=6 2E7, n=6 H2L1, (p<0.001 for each test compound vs. vehicle).

This data provides further evidence that the humanised H2L1 antibody has retained the functional properties shown with the mouse 2E7 molecule.

Investigation of the Pharmacokinetics of H2L1 and 2E7

The terminal half life of test antibody in mice was investigated. Test antibody was administered by a 1 h intravenous infusion to 4 mice to achieve a target dose of 400 ug per mouse. Serial blood samples were taken from each mouse up to 5 days after dosing (one mouse from the 2E7 group did not complete the study and one from the H2L1 group was removed from subsequent analysis because it became apparent the dose had not been administered i.v.). Antibody levels were measured using a β-amyloid capture ELISA.

Analysis of the data indicates that the humanised antibody H2L1 has a terminal half life of circa 82 hours in mice (Table 11), which is comparable to that of the parent mouse monoclonal antibody 2E7 (circa 75 hours).

TABLE 11

| Parameter | Mean ± SD (n = 3) |
|---|---|
| Cmax (ug/mL) | 291 ± 43 |
| Tmax (h) # | 2.0 (1.1-2.1) |
| CLp (mL/h/kg) | 0.9 ± 0.1 |
| t½ (h) | 82 ± 4 |
| Vss (mL/kg) | 94 ± 12 |

\# median and range
Cmax Observed maximum plasma concentration.
Tmax Time of the observed maximum plasma concentration
CLp Total plasma clearance; Dose/$AUC_{(0\text{-}inf)}$.
t½ Terminal phase half-life was determined as the ratio of ln2/z where z is the terminal phase rate constant; calculated using unweighted linear regression analysis (after log transformation) on those concentration-time pairs occurring after the visually assessed onset of the terminal log-linear phase.
Vss Volume of distribution at steady-state; CLp × $MRT_{0\text{-}inf}$.

Production Process

Expression vectors encoding H2L1 and operatively linked to amplifiable selection markers such as the DHFR or glutamine synthetase may be used to transfect or transduce appropriate parental CHO cell lines (eg CHODG44 or CHOK 1) to produce engineered cell lines suitable for production of monoclonal antibody at large scale (for review see Bebbington and Hentschel DNA Cloning Volume III; A practical approach (edited by Glover D M) (Oxford IRL press, 1987). In order to increase expression levels the coding sequence maybe codon optimized in order to avoid cis-acting sequence motifs and extreme GC contents (high or low). SEQ. ID Nos:42 and No:43 exemplify such a coding sequence for H2 heavy chain and L1 light chain. Large scale production maybe in stirred tank bioreactors using animal-derived-component-free medium, followed by purification. This may comprise clarification of the harvest, followed by Protein-A affinity chromatography, and further purification using ion (e.g. cation) exchange and mixed mode (e.g. ceramic hydroxyapatite) chromatography unit operations. A virus removal nanofiltration is followed by a final ultrafiltration/diafiltration step that enables formulation suitable for the intended route of administration.

Example of Pharmaceutical Formulation

| Ingredient | Quantity (per mL) |
| --- | --- |
| H2L1 | 50 mg |
| Sodium acetate trihydrate | 6.81 mg |
| Polysorbate 80 | 0.20 mg |
| Arginine base | 10.00 mg |
| Sodium chloride | 3.00 mg |
| Disodium edetate dihydrate | 0.0186 mg |
| Hydrochloric acid | qs to give pH 5.5 |
| Water for Injections | To make 1.0 mL |
| Nitrogen | To fill headspace |

Demonstration of Therapeutic Antibody Binding to Aβ in Drusen by Immunohistochemistry.

To demonstrate that the therapeutic antibody would help to bind and potentially clear or disrupt the Aβ present in drusen of human patients clinically diagnosed with AMD, patient samples could be obtained from an eye bank and binding to the Aβ found in drusen could be confirmed by standard immunohistochemistry. Tissue specimens of eyes could be obtained and subject to fixation as rapidly as possible post-mortem. Tissue could be obtained from "normal" eyes and donors clinically diagnosed with early AMD, geographic atrophy and exudative AMD. Sections could be cut and analysed by standard procedures for drusen presence, amyloid histochemistry and Aβ presence, e.g. Aβ could be confirmed by the use of Thioflavin T (Sigma). Therapeutic antibody binding to the Aβ in drusen could be monitored by either standard microscopy or laser scanning confocal microscopy. Therapeutic antibody could be labelled using standard procedures and used as the primary antibody to probe sections of fixed embedded eye tissue, or unlabelled therapeutic antibody could be used as a primary antibody and detected with a labelled secondary anti-human IgG antibody. Negative controls may be confirmed for non-specific labelling, including: omission of primary antibody, substitution with a similar concentration of irrelevant primary antibody or non-immune sera, and substitution with an inappropriate secondary antibody. Additionally where possible the autofluorescence of lipofuscin derived from the RPE tissue or from Bruch's membrane can be visualised to help place drusen structures in the eye (Anderson D H et al., (2004) Exp Eye Res 78: 243-256).

Demonstration of Therapeutic Antibody Binding to Aβ in Drusen by ELISA.

An ELISA could be performed to help determine binding of therapeutic antibody to Aβ in drusen. Eye tissue homogenates could be processed from drusen containing donors with AMD sources as described above. Processed eye tissues could be homogenised and the supernatant could be collected and the samples used to coat the wells of a standard 96 well ELISA plate. A standard ELISA could be performed using the therapeutic antibody as a primary antibody (either labelled or unlabelled). An enzyme-tagged secondary antibody to the primary or binding reagent to its label could then be used to mediate a standard ELISA colormetric read out. Increasing protein sample amounts should lead to an increasing Aβ-positive signal. Irrelevant primary antibodies at the same concentration of the same humanised IgG1 subclass may be used as a negative in such an experiment (Luibl et al (2006)).

Amino Acid Sequences of V-regions of Acceptor Frameworks and Humanised Variants

M99675 heavy chain acceptor framework V region, amino acid sequence
(SEQ ID No: 21)
EVQLVESGGGLVQPGGSLRLSCAASGFTFS<u>SYSMN</u>WVRQAPGKGLEWVS<u>Y</u>

<u>ISSSSSTI</u>YYADSVKGRFTISRDNAKNSLYLQMNSLRAEDTAVYYCAR

M99675 heavy chain acceptor framework V region DNA
(SEQ ID No: 22)
GAGGTGCAGCTGGTGGAGTCTGGGGGAGGCTTGGTACAGCCTGGGGGGTC

CCTGAGACTCTCCTGTGCAGCCTCTGGATTCACCTTCAGTAGCTATAGCA

TGAACTGGGTCCGCCAGGCTCCAGGGAAGGGGCTGGAGTGGGTTTCATAC

ATTAGTAGTAGTAGTAGTACCATATACTACGCAGACTCTGTGAAGGGCCG

ATTCACCATCTCCAGAGACAATGCCAAGAACTCACTGTATCTGCAAATGA

ACAGCCTGAGAGCCGAGGACACGGCTGTGTATTACTGTGCGAGAGA

CAA51135 light chain acceptor framework V region amino acid sequence
(SEQ ID No: 24)
DIVMTQSPLSLPVTPGEPASISC<u>RSSQSLLHSNGYNYLD</u>WYLQKPGQSPQ LLIY<u>LGSNRAS</u>GVPDRFSGSGSGTDFTLKISRVEAEDVGVYYC<u>MQALQTP</u>

<u>WT</u>FGQGTKVEIK

CAA51135 light chain acceptor framework V region DNA
(SEQ ID No: 25)
GATATTGTGATGACTCAGTCTCCACTCTCCCTGCCCGTCACCCCTGGAGA

GCCGGCCTCCATCTCCTGCAGGTCTAGTCAGAGCCTCCTGCATAGTAATG

GATACAACTATTTGGATTGGTACCTGCAGAAGCCAGGGCAGTCTCCACAG

CTCCTGATCTATTTGGGTTCTAATCGGGCCTCCGGGGTCCCTGACAGGTT

CAGTGGCAGTGGATCAGGCACAGATTTTACACTGAAAATCAGCAGAGTGG

AGGCTGAGGATGTTGGGGTTTATTACTGCATGCAAGCTCTACAAACTCCG

TGGACGTTCGGCCAAGGGACCAAGGTGGAAATCAAA

Humanised heavy chain V region variant H1, amino acid sequence
(SEQ ID No: 26)
EVQLVESGGGLVQPGGSLRLSCAASGFTFS<u>DNGMA</u>WVRQAPGKGLEWVS<u>F</u>

<u>ISNLAYSI</u>DYADTVTGRFTISRDNAKNSLYLQMNSLRAEDTAVYYCVS<u>GT</u>

<u>WFAY</u>WGQGTLVTVSS

Humanised heavy chain V region variant H1 DNA coding sequence
(SEQ ID No: 27)
GAGGTGCAGCTGGTGGAGTCTGGGGGAGGCTTGGTACAGCCTGGGGGGTC

CCTGAGACTCTCCTGTGCAGCCTCTGGATTCACCTTCAGTGACAACGGAA

TGGCGTGGGTCCGCCAGGCTCCAGGGAAGGGGCTGGAGTGGGTTTCATTC

```
ATTAGTAATTTGGCATATAGTATCGACTACGCAGACACTGTGACGGGCCG

ATTCACCATCTCCAGAGACAATGCCAAGAACTCACTGTATCTGCAAATGA

ACAGCCTGAGAGCCGAGGACACGGCTGTGTATTACTGTGTCAGCGGGACC

TGGTTTGCTTACTGGGGCCAGGGCACACTAGTCACAGTCTCCTCA
```
Humanised heavy chain V region variant H2,
amino acid sequence
(SEQ ID No: 28)
EVQLVESGGGLVQPGGSLRLSCAVSGFTFS<u>DNGMA</u>WVRQAPGKGLEWVS<u>F</u>

<u>ISNLAYSIDYADTVTG</u>RFTISRDNAKNSLYLQMNSLRAEDTAVYYCVS<u>GT</u>

<u>WFAY</u>WGQGTLVTVSS

Humanised heavy chain V region variant H2 DNA
(SEQ ID No: 29)
```
GAGGTGCAGCTGGTGGAGTCTGGGGGAGGCTTGGTACAGCCTGGGGGGTC

CCTGAGACTCTCCTGTGCAGTCTCTGGATTCACCTTCAGTGACAACGGAA

TGGCGTGGGTCCGCCAGGCTCCAGGGAAGGGGCTGGAGTGGGTTTCATTC

ATTAGTAATTTGGCATATAGTATCGACTACGCAGACACTGTGACGGGCCG

ATTCACCATCTCCAGAGACAATGCCAAGAACTCACTGTATCTGCAAATGA

ACAGCCTGAGAGCCGAGGACACGGCTGTGTATTACTGTGTCAGCGGGACC

TGGTTTGCTTACTGGGGCCAGGGCACACTAGTCACAGTCTCCTCA
```
Humanised heavy chain V region variant H3,
amino acid sequence
(SEQ ID No: 30)
EVQLVESGGGLVQPGGSLRLSCAASGFTFS<u>DNGMA</u>WVRQAPGKGLEWIS<u>F</u>

<u>ISNLAYSIDYADTVTG</u>RFTISRDNAKNSLYLQMNSLRAEDTAVYYCVS<u>GT</u>

<u>WFAY</u>WGQGTLVTVSS

Humanised heavy chain V region variant H3 DNA
(SEQ ID No: 31)
```
GAGGTGCAGCTGGTGGAGTCTGGGGGAGGCTTGGTACAGCCTGGGGGGTC

CCTGAGACTCTCCTGTGCAGCCTCTGGATTCACCTTCAGTGACAACGGAA

TGGCGTGGGTCCGCCAGGCTCCAGGGAAGGGGCTGGAGTGGATCTCATTC

ATTAGTAATTTGGCATATAGTATCGACTACGCAGACACTGTGACGGGCCG

ATTCACCATCTCCAGAGACAATGCCAAGAACTCACTGTATCTGCAAATGA

ACAGCCTGAGAGCCGAGGACACGGCTGTGTATTACTGTGTCAGCGGGACC

TGGTTTGCTTACTGGGGCCAGGGCACACTAGTCACAGTCTCCTCA
```
Humanised light chain V region variant L1
amino acid sequence
(SEQ ID No: 32)
DIVMTQSPLSLPVTPGEPASISC<u>RVSQSLLHSNGYTYLH</u>WYLQKPGQSPQ LLIY<u>KVSNRFS</u>GVPDRFSGSGSGTDFTLKISRVEAEDVGVYYC<u>SQTRHVP</u>

<u>YTF</u>GGGTKVEIK

Humanised light chain V region variant L1 DNA
(SEQ ID No: 33)
```
GATATTGTGATGACTCAGTCTCCACTCTCCCTGCCCGTCACCCCTGGAGA

GCCGGCCTCCATCTCCTGCAGAGTTAGTCAGAGCCTTTTACACAGTAATG

GATACACCTATTTACATTGGTACCTGCAGAAGCCAGGGCAGTCTCCACAG

CTCCTGATCTATAAAGTTTCCAACCGATTTTCTGGGGTCCCTGACAGGTT

CAGTGGCAGTGGATCAGGCACAGATTTTACACTGAAAATCAGCAGAGTGG

AGGCTGAGGATGTTGGGGTTTATTACTGCTCTCAAACTAGACATGTTCCG

TACACGTTCGGCGGAGGGACCAAGGTGGAAATCAAA
```
Mature H1 heavy chain amino acid sequence
(Fc mutated double mutation bold)
(SEQ ID No: 34)
EVQLVESGGGLVQPGGSLRLSCAASGFTFS<u>DNGMA</u>WVRQAPGKGLEWVS<u>F</u>

<u>ISNLAYSIDYADTVTG</u>RFTISRDNAKNSLYLQMNSLRAEDTAVYYCVS<u>GT</u>

<u>WFAY</u>WGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELAGAPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK

H1 Full length DNA
(SEQ ID No: 35)
```
GAGGTGCAGCTGGTGGAGTCTGG

GGGAGGCTTGGTACAGCCTGGGGGGTCCCTGAGACTCTCCTGTGCAGCCT
CTG

GATTCACCTTCAGTGACAACGGAATGG

CGTGGGTCCGCCAGGCTCCAGGGAAGGGGCTGGAGTGGGTTTCATTCATT
AGT

AATTTGGCATATAGTATCGACTACGCA

GACACTGTGACGGGCCGATTCACCATCTCCAGAGACAATGCCAAGAACTC
ACTG

TATCTGCAAATGAACAGCCTGAGAGC

CGAGGACACGGCTGTGTATTACTGTGTCAGCGGGACCTGGTTTGCTTACT
GGG

GCCAGGGCACACTAGTCACAGTCTCCT

CAGCCTCCACCAAGGGCCCATCGGTCTTCCCCCTGGCACCCTCCTCCAAG
AGC

ACCTCTGGGGGCACAGCGGCCCTGGGC

TGCCTGGTCAAGGACTACTTCCCCGAACCGGTGACGGTGTCGTGGAACTC
AGG

CGCCCTGACCAGCGGCGTGCACACCTT

CCCGGCTGTCCTACAGTCCTCAGGACTCTACTCCCTCAGCAGCGTGGTGA
CCG

TGCCCTCCAGCAGCTTGGGCACCCAGA

CCTACATCTGCAACGTGAATCACAAGCCCAGCAACACCAAGGTGGACAAG
AAA

GTTGAGCCCAAATCTTGTGACAAAACT

CACACATGCCCACCGTGCCCAGCACCTGAACTCGCGGGGGCACCGTCAGT
CTT

CCTCTTCCCCCCAAAACCCAAGGACAC

CCTCATGATCTCCCGGACCCCTGAGGTCACATGCGTGGTGGTGGACGTGA
GCC
```

```
ACGAAGACCCTGAGGTCAAGTTCAACT

GGTACGTGGACGGCGTGGAGGTGCATAATGCCAAGACAAAGCCGCGGGAG
GA

GCAGTACAACAGCACGTACCGTGTGGTC

AGCGTCCTCACCGTCCTGCACCAGGACTGGCTGAATGGCAAGGAGTACAA
GTG

CAAGGTCTCCAACAAAGCCCTCCCAGC

CCCCATCGAGAAAACCATCTCCAAAGCCAAAGGGCAGCCCCGAGAACCAC
AGG

TGTACACCCTGCCCCCATCCCGGGATG

AGCTGACCAAGAACCAGGTCAGCCTGACCTGCCTGGTCAAAGGCTTCTAT
CCCA

GCGACATCGCCGTGGAGTGGGAGAGC

AATGGGCAGCCGGAGAACAACTACAAGACCACGCCTCCCGTGCTGGACTC
CGA

CGGCTCCTTCTTCCTCTACAGCAAGCT

CACCGTGGACAAGAGCAGGTGGCAGCAGGGGAACGTCTTCTCATGCTCCG
TGA

TGCATGAGGCTCTGCACAACCACTACA

CGCAGAAGAGCCTCTCCCTGTCTCCGGGTAAA
```

Mature H2 heavy chain amino acid sequence,
(Fc mutated double mutation bold)
(SEQ ID No: 36)
EVQLVESGGGLVQPGGSLRLSCAVSGFTFS<u>DNGMA</u>WVRQAPGKGLEWVS<u>F</u>

<u>ISNLAYSIDYADTVTG</u>RFTISRDNAKNSLYLQMNSLRAEDTAVYYCVS<u>GT</u>

<u>WFAY</u>WGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELAGAPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK

H2 Full length DNA
(SEQ ID No: 37)
```
GAGGTGCAGCTGGTGGAGTCTGGGGGAGGCTTGGTACAGCCTGGGGGGTC
CC

TGAGACTCTCCTGTGCAGTCTCTGGATT

CACCTTCAGTGACAACGGAATGGCGTGGGTCCGCCAGGCTCCAGGGAAGG
GG

CTGGAGTGGGTTTCATTCATTAGTAATT

TGGCATATAGTATCGACTACGCAGACACTGTGACGGGCCGATTCACCATC
TCCA

GAGACAATGCCAAGAACTCACTGTAT

CTGCAAATGAACAGCCTGAGAGCCGAGGACACGGCTGTGTATTACTGTGT
CAG
```

```
CGGGACCTGGTTTGCTTACTGGGGCCA

GGGCACACTAGTCACAGTCTCCTCAGCCTCCACCAAGGGCCCATCGGTCT
TCC

CCCTGGCACCCTCCTCCAAGAGCACCT

CTGGGGGCACAGCGGCCCTGGGCTGCCTGGTCAAGGACTACTTCCCCGAA
CC

GGTGACGGTGTCGTGGAACTCAGGCGCC

CTGACCAGCGGCGTGCACACCTTCCCGGCTGTCCTACAGTCCTCAGGACT
CTA

CTCCCTCAGCAGCGTGGTGACCGTGCC

CTCCAGCAGCTTGGGCACCCAGACCTACATCTGCAACGTGAATCACAAGC
CCA

GCAACACCAAGGTGGACAAGAAAGTTG

AGCCCAAATCTTGTGACAAAACTCACACATGCCCACCGTGCCCAGCACCT
GAAC

TCGCGGGGCACCGTCAGTCTTCCTC

TTCCCCCCAAAACCCAAGGACACCCTCATGATCTCCCGGACCCCTGAGGT
CACA

TGCGTGGTGGTGGACGTGAGCCACGA

AGACCCTGAGGTCAAGTTCAACTGGTACGTGGACGGCGTGGAGGTGCATA
ATG

CCAAGACAAAGCCGCGGGAGGAGCAGT

ACAACAGCACGTACCGTGTGGTCAGCGTCCTCACCGTCCTGCACCAGGAC
TGG

CTGAATGGCAAGGAGTACAAGTGCAAG

GTCTCCAACAAAGCCCTCCCAGCCCCCATCGAGAAAACCATCTCCAAAGC
CAAA

GGGCAGCCCCGAGAACCACAGGTGTA

CACCCTGCCCCCATCCCGGGATGAGCTGACCAAGAACCAGGTCAGCCTGA
CCT

GCCTGGTCAAAGGCTTCTATCCCAGCG

ACATCGCCGTGGAGTGGGAGAGCAATGGGCAGCCGGAGAACAACTACAAG
AC

CACGCCTCCCGTGCTGGACTCCGACGGC

TCCTTCTTCCTCTACAGCAAGCTCACCGTGGACAAGAGCAGGTGGCAGCA
GGG

GAACGTCTTCTCATGCTCCGTGATGCA

TGAGGCTCTGCACAACCACTACACGCAGAAGAGCCTCTCCCTGTCTCCGG
GTA

AA
```

Mature H3 heavy chain amino acid sequence
(Fc mutated double mutation bold)
(SEQ ID No: 38)
EVQLVESGGGLVQPGGSLRLSCAASGFTFS<u>DNGMA</u>WVRQAPGKGLEWIS<u>F</u>

<u>ISNLAYSIDYADTVTG</u>RFTISRDNAKNSLYLQMNSLRAEDTAVYYCVS<u>GT</u>

<u>WFAY</u>WGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELAGAPSVFLFPPKPKDTLM

ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK

H3 full length DNA
(SEQ ID No: 39)
GAGGTGCAGCTGGTGGAGTCTGGGGGAGGCTTGGTACAGCCTGGGGGGTC
CCTGAGACTCTCCTGTGCAGCCTCTGGATTCACCTTCAGTGACAACGGAA
TGGCGTGGGTCCGCCAGGCTCCAGGGAAGGGGCTGGAGTGGATCTCATTC
ATTAGTAATTTGGCATATAGTATCGACTACGCAGACACTGTGACGGGCCG
ATTCACCATCTCCAGAGACAATGCCAAGAACTCACTGTATCTGCAAATGA
ACAGCCTGAGAGCCGAGGACACGGCTGTGTATTACTGTGTCAGCGGGACC
TGGTTTGCTTACTGGGGCCAGGGCACACTAGTCACAGTCTCCTCAGCCTC
CACCAAGGGCCCATCGGTCTTCCCCCTGGCACCCTCCTCCAAGAGCACCT
CTGGGGGCACAGCGGCCCTGGGCTGCCTGGTCAAGGACTACTTCCCCGAA
CCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGG
TGACCGTGCCCTCCAGCAGCTTGGGCACCCAGACCTACATCTGCAACGTG
AATCACAAGCCCAGCAACACCAAGGTGGACAAGAAAGTTGAGCCCAAATC
TTGTGACAAAACTCACACATGCCCACCGTGCCCAGCACCTGAACTCGCGG
GGGCACCGTCAGTCTTCCTCTTCCCCCCAAAACCCAAGGACACCCTCATG
ATCTCCCGGACCCCTGAGGTCACATGCGTGGTGGTGGACGTGAGCCACGA
AGACCCTGAGGTCAAGTTCAACTGGTACGTGGACGGCGTGGAGGTGCATA
ATGCCAAGACAAAGCCGCGGGAGGAGCAGTACAACAGCACGTACCGTGTG
GTCAGCGTCCTCACCGTCCTGCACCAGGACTGGCTGAATGGCAAGGAGTA
CAAGTGCAAGGTCTCCAACAAAGCCCTCCCAGCCCCCATCGAGAAAACCA
TCTCCAAAGCCAAAGGGCAGCCCCGAGAACCACAGGTGTACACCCTGCCC
CCATCCCGGGATGAGCTGACCAAGAACCAGGTCAGCCTGACCTGCCTGGT
CAAAGGCTTCTATCCCAGCGACATCGCCGTGGAGTGGGAGAGCAATGGGC
AGCCGGAGAACAACTACAAGACCACGCCTCCCGTGCTGGACTCCGACGGC
TCCTTCTTCCTCTACAGCAAGCTCACCGTGGACAAGAGCAGGTGGCAGCA
GGGGAACGTCTTCTCATGCTCCGTGATGCATGAGGCTCTGCACAACCACT
ACACGCAGAAGAGCCTCTCCCTGTCTCCGGGTAAA Mature Light chain amino acid sequence
(SEQ ID No: 40)
DIVMTQSPLSLPVTPGEPASISC<u>RVSQSLLHSNGYTYLH</u>WYLQKPGQSPQ
LLIY<u>KVSNRFS</u>GVPDRFSGSGSGTDFTLKISRVEAEDVGVYYC<u>SQTRHVP</u>
<u>YT</u>FGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE
VTHQGLSSPVTKSFNRGEC

L1 Full length DNA
(SEQ ID No: 41)
GATATTGTGATGACTCAGTCTCCACTCTCCCTGCCCGTCACCCCTGGAGA
GCCGGCCTCCATCTCCTGCAGAGTTAGTCAGAGCCTTTTACACAGTAATG
GATACACCTATTTACATTGGTACCTGCAGAAGCCAGGGCAGTCTCCACAG
CTCCTGATCTATAAAGTTTCCAACCGATTTTCTGGGGTCCCTGACAGGTT
CAGTGGCAGTGGATCAGGCACAGATTTTACACTGAAAATCAGCAGAGTGG
AGGCTGAGGATGTTGGGGTTTATTACTGCTCTCAAACTAGACATGTTCCG
TACACGTTCGGCGAGGGACCAAGGTGGAAATCAAACGTACGGTGGCTGC
ACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAA
GTACAGTGGAAGGTGGACAACGCCCTCCAATCGGGTAACTCCCAGGAGAG
TGTCACAGAGCAGGACAGCAAGGACAGCACCTACAGCCTCAGCAGCACCC
TGACGCTGAGCAAAGCAGACTACGAGAAACACAAAGTCTACGCCTGCGAA
GTCACCCATCAGGGCCTGAGCTCGCCCGTCACAAAGAGCTTCAACAGGGG
AGAGTGT Optimised H2 heavy chain DNA
(SEQ ID No: 42)
GAGGTGCAGCTGGTGGAGTCTGGCGGCGGACTGGTGCAGCCTGGCGGCAG
CCTGAGACTGAGCTGTGCCGTGTCCGGCTTCACCTTCAGCGACAACGGCA
TGGCCTGGGTGAGGCAGGCCCCTGGCAAGGGCCTGGAGTGGGTGTCCTTC
ATCAGCAACCTGGCCTACAGCATCGACTACGCCGACACCGTGACCGGCAG
ATTCACCATCAGCCGGGACAACGCCAAGAACAGCCTGTACCTGCAGATGA
ACAGCCTGAGAGCCGAGGACACCGCCGTGTACTACTGTGTGAGCGGCACC
TGGTTCGCCTACTGGGGCCAGGGCACCCTGGTGACCGTGTCCAGCGCCAG
CACCAAGGGCCCCAGCGTGTTCCCCCTGGCCCCCAGCAGCAAGAGCACCA
GCGGCGGCACAGCCGCCCTGGGCTGCCTGGTGAAGGACTACTTCCCCGAA
CCGGTGACCGTGTCCTGGAACAGCGGAGCCCTGACCAGCGGCGTGCACAC
CTTCCCCGCCGTGCTGCAGAGCAGCGGCCTGTACAGCCTGAGCAGCGTGG
TGACCGTGCCCAGCAGCAGCCTGGGCACCCAGACCTACATCTGTAACGTG
AACCACAAGCCCAGCAACACCAAGGTGGACAAGAAGGTGGAGCCCAAGAG
CTGTGACAAGACCCACACCTGCCCCCCCTGCCCTGCCCCCGAGCTGGCCG
GAGCCCCCAGCGTGTTCCTGTTCCCCCCCAAGCCTAAGGACACCCTGATG
ATCAGCAGAACCCCCGAGGTGACCTGTGTGGTGGTGGATGTGAGCCACGA
GGACCCTGAGGTGAAGTTCAACTGGTACGTGGACGGCGTGGAGGTGCACA
ATGCCAAGACCAAGCCCAGGGAGGAGCAGTACAACAGCACCTACCGGGTG
GTGTCCGTGCTGACCGTGCTGCACCAGGATTGGCTGAACGGCAAGGAGTA
CAAGTGTAAGGTGTCCAACAAGGCCCTGCCTGCCCCTATCGAGAAAACCA
TCAGCAAGGCCAAGGGCCAGCCCAGAGAGCCCCAGGTGTACACCCTGCCC
CCTAGCAGAGATGAGCTGACCAAGAACCAGGTGTCCCTGACCTGCCTGGT

```
-continued
GAAGGGCTTCTACCCCAGCGACATCGCCGTGGAGTGGGAGAGCAACGGCC

AGCCCGAGAACAACTACAAGACCACCCCCCCTGTGCTGGACAGCGATGGC

AGCTTCTTCCTGTACAGCAAGCTGACCGTGGACAAGAGCAGATGGCAGCA

GGGCAACGTGTTCAGCTGCTCCGTGATGCACGAGGCCCTGCACAATCACT

ACACCCAGAAGAGCCTGAGCCTGTCCCCTGGCAAG

Optimised L1 light chain DNA
                                            (SEQ ID No: 43)
GACATCGTGATGACCCAGAGCCCCCTGAGCCTGCCCGTGACCCCTGGCGA

GCCCGCCAGCATCAGCTGTAGAGTGAGCCAGAGCCTGCTGCACAGCAACG

GCTACACCTACCTGCACTGGTATCTGCAGAAGCCTGGCCAGAGCCCTCAG

CTGCTGATCTACAAGGTGTCCAACCGGTTCAGCGGCGTGCCTGATAGATT

CAGCGGCAGCGGCTCCGGCACCGACTTCACCCTGAAGATCAGCAGAGTGG

AGGCCGAGGATGTGGGCGTGTACTACTGCTCCCAGACCAGACACGTGCCT

TACACCTTTGGCGGCGGAACAAAGGTGGAGATCAAGCGTACGGTGGCCGC

CCCCAGCGTGTTCATCTTCCCCCCCAGCGATGAGCAGCTGAAGAGCGGCA

CCGCCAGCGTGGTGTGTCTGCTGAACAACTTCTACCCCGGGAGGCCAAG

GTGCAGTGGAAGGTGGACAATGCCCTGCAGAGCGGCAACAGCCAGGAGAG

CGTGACCGAGCAGGACAGCAAGGACTCCACCTACAGCCTGAGCAGCACCC

TGACCCTGAGCAAGGCCGACTACGAGAAGCACAAGGTGTACGCCTGTGAG

GTGACCCACCAGGGCCTGTCCAGCCCCGTGACCAAGAGCTTCAACCGGGG

CGAGTGC
```

REFERENCES

Anderson D H, Talaga K C, Rivest A J, Barron E, Hageman G S, Johnson L V (2004) Exp Eye Res 78: 243-256

Bard F, Cannon C, Barbour R, Burke R L, Games D, Grajeda H, Guido T, Hu K, Huang J, Johnson-Wood K, Khan K, Kholodenko D, Lee M, Lieberburg I, Motter R, Nguyen M, Soriano F, Vasquez N, Weiss K, Welch B, Seubert P, Schenk D, Yednock T (2000) Nature 6:916-919

Baumritter A, Clark C M, Martin R, Steinberg J D, Stoltz R A, Ying G S, Brightwell-Arnold M, Maguire M G (2007) Association for Research in Vision and Opthalmology, (ARVO) Meeting: "The Aging Eye" May 6th-10th, Fort Lauderdale, Fla. USA, Poster Presentation 2092/B701

Birch D G, Liang F Q, (2007) Int J Nanomed 2:65-77

Bowes Rickman C, (2007), 11th Annual Vision Research Conference: Retinal Degeneration and Gene Therapy, 4th-5th May, Fort Lauderdale, Fla. USA, Oral presentation O4.4

Cheung Z H, Chan Y-M, F K W Siu, H K Yip, W Wu, M C P Leung, K-F So (2004) Mol Cell Neurosci 25:383-393

Cordeiro M F, Guo L, Luong V, Harding G, Wang W, Jones H E, Moss S E, Sillito A M, Fitzke F W (2004) Proc Natl Acad Sci USA 101:13352-13356

Deane R, Sagare A, Hamm K, Parisi M, LaRue B, Guo H, Wu Z, Holtzman D M, Zlokovic B V (2005) J Neuroscience 25:11495-11503

Deane R, Zlokovic B V (2007) Curr Alzheimer Res 4:191-197

DeMattos R B, Bales K R, Cummins D J, Paul S M, Holtzman D M (2002) Science 295:2264-2267

Dentchev T, Milam A H, Lee V M Y, Trojanowski J Q, Dunaief J L (2003) Mol Vision 9: 184-190

Ding J D, Lin J, Mace B E, Herrmann R, Sullivan P, Bowes Rickman C (2008) Vision Research, 48: 339-345

Goldstein L E, Muffat J A, Cherny R A, Moir R D, Ericsson M H, Huang X, Mavros C, Coccia J A, Faget K Y, Fitch K A, Masters C L, Tanzi R E, Chylack L T, Bush Al, (2003) Lancet 361: 1258-1265

Guo L, Salt T E, Luong V, Wood N, Cheung W, Maas A, Ferrari G, Russo-Marie F, Sillito A M, Cheetham M E, Moss S E, Fitzke F W, Cordeiro M F (2007) Proc Natl Acad Sci USA 104:13444-13449

Hageman G S, Luthert P J, Chong N H V, Johnson L V, Anderson D H, Mullins R F (2001) Prog Ret Eye Res 20: 705-732

He X, Cooley K, Chung C H Y, Dashti N, Tang J (2007) J Neurosci 27: 4052-4060

Janoira K G, Gunda S, Boddu S H S, Mitra A K, (2007) Expert Opin Drug Deliv 4: 371-388

Johnson L V, Leitner W P, Staples M K, Anderson D H (2001) Exp Eye Res 73: 887-896

Johnson L V, Leitner W P, Rivest A J, Staples M K, Radeke M J, Anderson D H (2002) PNAS USA 99: 11830-11835

Klaver C C, Ott A, Hofman A, Assink J J, Breteler M M, de Jong (1999) Am J Epidemiol 150: 963-968

Kliffen M, Lutgens E, Daemen M J A P, de Muinck E D, Mooy C M, de Jong P T V M (2000) Br J Opthalmology 84: 1415-1419

Li G, Percontino L, Sun Q, Qazi A S, Frederikse P H, (2003) Mol Vision 9: 179-183

Luibl V, Isas J M, Kayed R, Glabe C G, Langen R, Chen J (2006) J Clin Invest 116: 378-385

Malek G, Johnson L V, Mace B E, Saloupis P, Schmechel D E, Rickman D W, Toth C A, Sullivan P M, Bowes Rickman C (2005) PNAS USA 102: 11900-11905

McKinnon S J, Lehman D M, Kerrigan-Baumrind L A, Merges C A, Pease M E, Kerrigan D F, Ransom N L, Tahzib N G, Reitsamer H A, Levkovitch-Verbin H et al (2002) Invest Ophtalmol Visual Sci 43:1077-1087

Mullins R F, Russell S R, Anderson D H, Hageman G S (2000) FASEB J 14: 835-846 Loeffler K, Edward D, Tso M (1995) Invest Opthalmol Vis Res 36: 24-31

Oliver J E, Hattenhauer M G, Herman D, Hodge D O, Kennedy R, Fang-Yen M, Johnson D H (2002) Am J Ophtamol 133:764-772

Petrukhin K (2007) Expert Opin Ther Targets 11: 625-639

Quigley H A, Nickells R W, Kerrigan L A, Pease M E, Thibault D J, Zack D J (1995) Invest Ophtalmol Visual Sci 36:774-786

Rakover I, Arbel M, Solomon B (2006) Neurodegenerative Dis 4:392-402

Ricklin, D & Lambris, J. (2007) Nature Biotechnology 25:1265-75.

Rodrigues E (2007) Opthalmologica 221: 143-152

Shibata M, Yamada S, Kumar S R, Calero M, Bading J, Frangione B, Holtzman D M, Miller C A, Strickland D K, Ghiso J, Zlokovic B V (2000) J Clin Invest 106: 1489-1499

Terai K, Iwai A, Kawabata S, Tasaki Y, Watanabe T, Miyata K, Yamaguchi T (2001) Neuroscience 104: 299-310

Williams K A, Bereton H M, Farrall A, Standfield S D, Taylor S D, Kirk L A, Coster D J (2005) Eye 19; 910-913

Yang S P, Bae D G, Kang H J, Gwag B J, Gho Y S, Chae C B (2004) Neurobiol Aging 25:283-290

Yoshida T, Ohno-Matsui K, Ichinose S, Sato T, Iwata N, Saido T C, Hisatomi T, Mochizuki M, Morita 1 (2005) J Clin Invest 115: 2793-2800

Zlokovic B V (2004) J Neurochem 89:807-811.

The invention claimed is:

1. A method of treating a human patient afflicted with age-related macular degeneration (AMD), glaucoma or β-amyloid dependent cataract formation, which method comprises the step of administering to said patient a therapeutically effective amount of an antibody or antigen binding fragment and/or derivative thereof which binds β-antyloid peptide and which comprises the following CDRs:

| | | |
|---|---|---|
| CDRH1: | DNGMA | (SEQ ID No: 1) |
| CDRH2: | FISNLAYSIDYADTVTG | (SEQ ID No: 2) |
| CDRH3: | GTWFAY | (SEQ ID No: 3) | within a human heavy chain variable region originating from the VH3 gene family and:

| | | |
|---|---|---|
| CDRL1: | RVSQSLLHSNGYTYLH | (SEQ ID No: 4) |
| CDRL2: | KVSNRFS | (SEQ ID No: 5) |
| CDRL3: | SQTRHVPYT | (SEQ ID No: 6) | within a human light chain variable region originating from the amino acid sequence disclosed in GenPept entry GAAS1135 (SEQ ID No:241).

2. A method of treating a human patient afflicted with age-related macular degeneration (AMD) which method comprises the step of administering to said patient a therapeutically effective amount of an antibody or antigen binding fragment and/or derivative thereof which hinds β-amyloid peptide and which comprises the following CDRs:

| | | |
|---|---|---|
| CDRH1: | DNGMA | (SEQ ID No: 1) |
| CDRH2: | FISNLAYSIDYADTVTG | (SEQ ID No: 2) |
| CDRH3: | GTWFAY | (SEQ ID No: 3) | within a human heavy chain variable region originating from the VH3 gene family and:

| | | |
|---|---|---|
| CDRL1: | RVSQSLLHSNGYTYLH | (SEQ ID No: 4) |
| CDRL2: | KVSNRFS | (SEQ ID No: 5) |
| CDRL3: | SQTRHVPYT | (SEQ ID No: 6) | within a human light chain variable region originating from the amino acid sequence disclosed in GenPept entry CAA51135 (SEQ ID No:24).

3. A method as claimed in claim 2 wherein the antibody comprises a heavy chain variable region having the sequence set forth in SEQ ID No:28 and a light chain variable region having the sequence set forth in SEQ ID No:32.

4. A method as claimed in claim 2 wherein the antibody comprises a heavy chain having the sequence set forth in SEQ ID No:34, 36 or 38 and a light chain having the sequence set forth in SEQ ID No:40.

5. A method of treating a human patient afflicted with glaucoma which method comprises the step of administering to said patient a therapeutically effective amount of an antibody or antigen binding fragment and/or derivative thereof which binds β-amyloid peptide and which comprises the following CDRs:

| | | |
|---|---|---|
| CDRH1: | DNGMA | (SEQ ID No: 1) |
| CDRH2: | FISNLAYSIDYADTVTG | (SEQ ID No: 2) |
| CDRH3: | GTWFAY | (SEQ ID No: 3) | within a human heavy chain variable region originating from the VH3 gene family and:

| | | |
|---|---|---|
| CDRL1: | RVSQSLLHSNGYTYLH | (SEQ ID No: 4) |
| CDRL2: | KVSNRFS | (SEQ ID No: 5) |
| CDRL3: | SQTRHVPYT | (SEQ ID No: 6) | within a human light chain variable region originating from the amino acid sequence disclosed in GenPept entry CAA51135 (SEQ ID No:24).

6. A method as claimed in claim 5 wherein the antibody comprises a heavy chain variable region having the sequence set forth in SEQ ID No:28 and a light chain variable region having the sequence set forth in SEQ ID No:32.

7. A method as claimed in claim 5 wherein the antibody comprises a heavy chain having the sequence set forth in SEQ ID No:34, 36 or 38 and a light chain having the sequence set forth in SEQ ID No:40.

8. A method of treating a human patient afflicted with β-amyloid dependent cataract formation which method comprises the step of administering to said patient a therapeutically effective amount of an antibody or antigen binding fragment and/or derivative thereof which binds β-amyloid peptide and which comprises the following CDRs:

```
CDRH1:   DNGMA              (SEQ ID No: 1)
CDRH2:   FISNLAYSIDYADTVTG  (SEQ ID No: 2)
CDRH3:   GTWFAY             (SEQ ID No: 3)
``` within a human heavy chain variable region originating from the VH3 gene family and:

```
CDRL1:   RVSQSLLHSNGYTYLH   (SEQ ID No: 4)
CDRL2:   KVSNRFS            (SEQ ID No: 5)
CDRL3:   SQTRHVPYT          (SEQ ID No: 6)
``` within a human light chain variable region originating from the amino acid sequence disclosed in GenPept entry CAA51135 (SEQ ID No:24).

9. A method as claimed in claim 8 wherein the antibody comprises a heavy chain variable region having the sequence set forth in SEQ ID No:28 and a light chain variable region having the sequence set forth in SEQ ID No:32.

10. A method as claimed in claim 8 wherein the antibody comprises a heavy chain having the sequence set forth in SEQ ID No:34, 36 or 38 and a light chain having the sequence set forth in SEQ ID No:40.

* * * * *